United States Patent
Chan et al.

(10) Patent No.: US 11,197,911 B2
(45) Date of Patent: Dec. 14, 2021

(54) PEPTIDYLIC INHIBITORS TARGETING C9ORF72 HEXANUCLEOTIDE REPEAT-MEDIATED NEURODEGENERATION

(71) Applicant: The Chinese University of Hong Kong, Hong Kong (CN)

(72) Inventors: Ho Yin Edwin Chan, Shatin (CN); Jacky Chi-Ki Ngo, Kowloon (CN); Qian Zhang, Shatin (CN)

(73) Assignee: The Chinese University of Hong Kong, Hong Kong (CN)

( * ) Notice: Subject to any disclaimer, the term of this patent is extended or adjusted under 35 U.S.C. 154(b) by 1078 days.

(21) Appl. No.: 15/802,070

(22) Filed: Nov. 2, 2017

(65) Prior Publication Data

US 2018/0214515 A1    Aug. 2, 2018

Related U.S. Application Data

(60) Provisional application No. 62/416,492, filed on Nov. 2, 2016.

(51) Int. Cl.
    A61K 38/17     (2006.01)
    A61K 45/06     (2006.01)
    A61K 9/00      (2006.01)

(52) U.S. Cl.
    CPC ........ *A61K 38/1709* (2013.01); *A61K 9/0019* (2013.01); *A61K 45/06* (2013.01)

(58) Field of Classification Search
    CPC ............................ A61K 38/1709; A61K 45/06
    See application file for complete search history.

(56) References Cited

PUBLICATIONS

Su et al., "Discovery of a Biomarker and Lead Small Molecules to Target r(GGGGCC)-Associated Defects in c9FTD/ALS", Neuron, 2014 85(5):1043-1050 (Year: 2014).*
Arumugam, et al., "Solution structure of the RBD1,2 domains from human nucleolin," J Biomol NMR (2010) 47:79-83.
Avitabile et al., "Nucleolar stress is an early response to myocardial damage involving nucleolar proteins nucleostemin and nucleophosmin," PNAS, vol. 108, No. 15, Apr. 12, 2011, 6145-6150.
Banez-Coronel et al., "A Pathogenic Mechanism in Huntington's Disease Involves Small CAG-Repeated RNAs with Neurotoxic Activity," PloS Genetics, vol. 8, Issue 2, Feb. 2012, 15 pages.
Beck et al., "Large C9orf72 Hexanucleotide Repeat Expansions Are Seen in Multiple Neurodegenerative Syndromes and Are More Frequent Than Expected in the UK Population," The American Journal of Human Genetics 92, Mar. 7, 2013, 345-353.
Belzil, et al., "Reduced C9orf72 gene expression in C9FTD/ALS is caused by histone trimethylation, an epigenetic event detectable in blood," Acta Neuropathol (2013) 126:895-905.
Daubner et al., "RRM-RNA recognition: NMR or crystallography . . . and new findings," Current Opinion in Structural Biology 2013, 23:100-108.
Dejesus-Hernandez, et al., "Expanded GGGGCC Hexanucleotide Repeat in Noncoding Region of C9ORF72 Causes Chromosome 9p-Linked FTD and ALS," Neuron 72, Oct. 20, 2011, 245-256.
Donnelly, et al., RNA Toxicity from the ALS/FTD C9ORF72 Expansion Is Mitigated by Antisense Intervention, Neuron 80, Oct. 16, 2013, 415-428.
Fawell, et al., Tat-mediated delivery of heterologous proteins into cells, Cell Biology, Proc. Natl. Acad. Sci. USA 91 (1994), 5 pages.
Frankel et al., " Cellular Uptake fo the Tat Protein from Humna Immunodeficiency Virus," Cell, vol. 55, Dec. 23, 1988, 1189-1193.
Gendron et al., "Antisense transcripts of the expanded C9ORF72 hexanucleotide repeat form nuclear RNA foci and undergo repeat-associated non-ATG translation in c9FTD/ALS," Acta Neuropathol (2013) 126:829-844.
Green et al., "Autonomous Functional Domains of Chemically Synthesized Human Immunodeficiency Virus Tat Trans-Activator Protein," Cell, vol. 55, Dec. 23, 1988, 1179-1188.
Haeusler et al., "C9orf72 nucleotide repeat structures initiate molecular cascades of disease," Nature, vol. 507, Mar. 13, 2014, 20 pages.
Kearse et al., "Repeat-Associated Non-AUG Translation and Its Impact in Neurodegenerative Disease," Neurotherapeutics (2014) 11:721-731.
Lee et al., "Hexanucleotide Repeats in ALS/FTD Form Length-Dependent RNA Foci, Sequester RNA Binding Proteins, and Are Neurotoxic," Cell Reports 5, Dec. 12, 2013, 1178-1186.
Linford, et al., "Measurement of Lifespan in *Drosophila melanogaster*," Journal of Visualized Experiments, 71, Jan. 2013, 9 pages.
Majounie et al., "Frequency of the C9orf72 hexanucleotide repeat expansion in patients with amyotrophic lateral sclerosis and frontotemporal dementia: a cross-sectional study," Lancet Neurol, vol. 11, Apr. 2012, 323-330.
Mori et al., "Bidirectional transcripts of the expanded C9orf72 hexanucleotide repeat are translated into aggregating dipeptide repeat proteins," Acta Neuropathol (2013) 126:881-893.
Mizielinska, et al., "C9orf72 repeat expansions cause neurodegeneration in *Drosophila* through arginine-rich proteins,"Science, vol. 345, Issue 6201, Sep. 5, 2014, 1192-1194.
Parlato et al., "Nucleolar activity in neurodegenerative diseases: a missing piece of the puzzle?," J Mol Med (2013) 91:541-547.
Renton et al., "A Hexanucleotide Repeat Expansion in C9ORF72 Is the Cause of Chromosome 9p21-Linked ALS-FTD," Neuron 72, Oct. 20, 2011, 257-268.
Rickards et al., "Nucleolin Is Required for RNA Polymerase I Transcription In Vivo," Molecular and Cellular Biology, Feb. 2007, p. 937-948.
Shaltiel-Karyo, et al., "A Novel, Sensitive Assay for Behavioral Defects in Parkinson's DiseaseModel *Drosophila*," Parkinson's Disease, vol. 2012, Article ID 697564, 6 pages.
Tao et al., "Nucleolar stress and impaired stress granule formation contribute to C9orf72 RAN translation-induced cytotoxicity," Human Molecular Genetics, 2015, vol. 24, No. 9, 2426-2441.

(Continued)

*Primary Examiner* — Lianko G Garyu
(74) *Attorney, Agent, or Firm* — Kilpatrick Townsend & Stockton LLP

(57) ABSTRACT

The present invention provides for a novel peptide inhibitor and method for treating neurological disorders related to a hexanucleotide (GGGGCC) repeat expansion in the non-coding region of the C9ORF72 gene. Also disclosed are related compositions and kits for therapeutic use in the treatment of the pertinent diseases.

10 Claims, 5 Drawing Sheets

Specification includes a Sequence Listing.

(56) References Cited

PUBLICATIONS

Van Blitterswijk, et al., "Association between repeat sizes and clinical and pathological characteristics in carriers of C9ORF72 repeat expansions (Xpansize-72): a cross-sectional cohort study," Lancet Neurol 2013; 12: 978-88.

Vatovec et al., "Unconventional features of C9ORF72 expanded repeat in amyotrophic lateral sclerosis and frontotemporal lobar degeneration," Neurobiology of Aging 35 (2014) 2421.e1e2421.e12.

Vives et al., "A Truncated HIV-1 Tat Protein Basic Domain Rapidly Translocates through the Plasma Membrane and Accumulates in the Cell Nucleus," The Journal of Biological Chemistry vol. 272, No. 25, Issue of Jun. 20, 1997, p. 16010-16017.

Wang et al., "p53 and Mitochondrial Function in Neurons," Biochim Biophys Acta. Aug. 2014; 1842(8): 1186-1197.

Yao et al., "B23 acts as a nucleolar stress sensor and promotes cell survival through its dynamic interaction with hnRNPU and hnRNPA1," Oncogene (2010) 29, 1821-1834.

Zhang et al., "Signaling to p53: Ribosomal Proteins Find Their Way," Cancer Cell 16, Nov. 3, 2009, 9 pages.

Zhang et al., "Assessing a peptidylic inhibitor-based therapeutic approach that simultaneously suppresses polyglutamine RNA- and proteinmediated toxicities in patient cells and *Drosophila*," Disease Models & Mechanisms (2016) 9, 321-334.

Zu et al., "Non-ATG-initiated translation directed by microsatellite expansions," PNAS, vol. 108, No. 1, Jan. 4, 2011, 260-265.

\* cited by examiner

PEPTIDYLIC INHIBITORS TARGETING C9ORF72 HEXANUCLEOTIDE REPEAT-MEDIATED NEURODEGENERATION

RELATED APPLICATIONS

This application claims priority to U.S. Provisional Application No. 62/416,492, filed Nov. 2, 2016, the contents of which are hereby incorporated by reference in the entirety for all purposes.

REFERENCE TO SUBMISSION OF A SEQUENCE LISTING AS A TEXT FILE

The Sequence Listing written in file SEQ_080015-1060387-020810US_ST25.txt created on Mar. 23, 2018, 11,840 bytes, machine format IBM-PC, MS-Windows operating system, is hereby incorporated by reference in its entirety for all purposes.

BACKGROUND OF THE INVENTION

Many neurodegenerative diseases, including Alzheimer's and Parkinson's diseases, are caused by protein misfolding. Cellular proteins that adopt abnormal pathogenic conformations oligomerize and subsequently form soluble and/or insoluble aggregates in cells causing neuronal dysfunction and death. Frontotemporal dementia (FTD) and amyotrophic lateral sclerosis (ALS) are thought to belong to a spectrum of neurodegenerative disorders with shared clinicopathological and genetic features. Recent studies have identified a class of disorders collectively termed c9FTD/ALS, which are caused by GGGGCC hexanucleotide repeat (SEQ ID NO:12) expansions in the chromosome 9 open-reading frame 72 (C9orf72) gene. It has recently been reported that an unconventional mechanism of repeat-associated non-ATG (RAN) translation arises from the expansion of the GGGGCC hexanucleotide repeat in the C9orf72 gene. Sense and antisense transcripts of the expanded C9orf72 repeat, i.e., the dipeptide repeat protein (DRP) of glycine-alanine (poly-GA), glycine-proline (poly-GP), glycine-arginine (poly-GR), proline-arginine (poly-PR), and proline-alanine (poly-PA), are found deposited in the brains of c9FTD/ALS patients. The expression of these polypeptides, especially the poly-GR or poly-PR peptides, is believed to be associated to caspase-3 activation, impaired neurite outgrowth, inhibition of protease activity, and endoplasmic reticulum (ER) stress, therefore contributing to neurotoxicity in c9FTD/ALS. To this day, however, the precise pathological significance of RAN-translated peptides in the development and progression of c9FTD/ALS remains to be fully illustrated.

In view of the prevalence and devastating effects of neurodegenerative disorders such as c9FTD/ALS, there exists a pressing need to develop new and effective methods and compositions for treating neurological diseases and disorders involving GGGGCC expansion in the non-coding region of the C9orf72 gene by reducing or eliminating cytotoxicty induced by the expanded GGGGCC-RNA or poly-GA peptide molecules. This invention fulfills this and other related needs.

BRIEF SUMMARY OF THE INVENTION

The present inventors surprisingly discovered that certain fragments of the nucleolin protein (NCL) can directly interact with GGGGCC-repeat RNA and suppress GGGGCC-repeat RNA toxicity. Thus, this invention provides novel methods and compositions useful for treating a neurodegenerative disease related to GGGGCC expension in the C9orf72 gene upstream non-coding sequence, such as the C9orf71 gene caused frontotemporal dementia and amyotrophic lateral sclerosis (C9FTD/ALS).

In the first aspect, the present invention provides an isolated polypeptide useful for treating a poly(GA) disease. The polypeptide comprising (1) a core sequence, which is a fragment of the NCL protein comprising SEQ ID NO:1 (AEIRLVSKDGKSKGIAYIEFK); and (2) a heterologous amino acid sequence, provided that the polypeptide does not comprise the full length NCL protein. In some embodiments, the heterologous amino acid sequence is a cell penetrating peptide, such as TAT peptide (e.g., having the amino acid sequence of SEQ ID NO:6). In some embodiments, the core amino acid sequence is SEQ ID NO:1. In some embodiments, the polypeptide consists of SEQ ID NO:1 and a TAT peptide, with the TAT peptide located at the N-terminus of the polypeptide and SEQ ID NO:1 located at the C-terminus of the polypeptide.

In a related aspect, the present invention provides a composition useful for the treatment of a poly(GA) disease. The composition comprises the polypeptide described above and herein along with a physiologically acceptable excipient. In some embodiments, the polypeptide consists of SEQ ID NO:1 and a TAT peptide, which is at the N-terminus of the polypeptide. In some embodiments, the polypeptide further comprises another therapeutic agent effective for treating a poly(GA) disease, for example, antisense oligonucleotides or small molecules (see, e.g., Donnelly et al., Neuron 2013 80(2):415-428; Su et al., Neuron 2014 85(5):1043-1050).

In a second aspect, the present invention provides a method for treating a poly(GA) disease in a subject. The method involves a step of administering to the subject an effective amount of a polypeptide comprising an NCL RRM domain. This polypeptide encompasses a fragment of NCL comprising SEQ ID NO:1 but does not encompass the full length NCL. This polypeptide optionally further comprises one or more heterologous amino acid sequences, which may be located at the N-terminus and/or C-terminus of the polypeptide. Even with the addition of the heterologous amino acid sequence(s), this polypeptide does not include a full length NCL sequence. In some cases, the heterologous amino acid sequence is a cell-penetrating peptide, such as a TAT peptide.

In some embodiments, the polypeptide consists of SEQ ID NO:1 and a TAT peptide, which is at the N-terminus of the polypeptide. In some embodiments, another therapeutic agent effective for treating a poly(GA) disease is co-administered to the patient. Such agent may be an inhibitor of expanded GGGGCC RNA toxicity or poly(GA) protein toxicity, such as antisense oligonucleotides or small molecules (see, e.g., Donnelly et al., Neuron 2013 80(2):415-428; Su et al., Neuron 2014 85(5):1043-1050). In some embodiments, the polypeptide is administered orally or by injection intravenously, intramuscularly, or subcutaneously, intraperitoneally. In some embodiments, the polypeptide is administered once daily, weekly, or monthly. Frequently, about 1-10,000 mg, about 10-1,000 mg, about 10-100 mg, about 20-50 mg, or about 10, 20, 30, 40, or 50 mg of the polypeptide is administered each time to the subject per kg of the subject's body weight. In practicing the method, the subject often has been diagnosed with a poly(GA) disease or is at risk of developing a poly(GA) disease.

In a related aspect, the present invention indicates the use of a polypeptide comprising an NCL RRM domain in the manufacture of a medicament for treating a poly(GA) disease in a subject. As described herein, this polypeptide encompasses a fragment of NCL comprising SEQ ID NO:1 but does not encompass the full length NCL. This polypeptide optionally may further comprise one or more heterologous amino acid sequences, which can be located at the N-terminus and/or C-terminus of the polypeptide. Even with the addition of the heterologous amino acid sequence(s), this polypeptide does not include a full length NCL sequence. In some cases, the heterologous amino acid sequence is a cell-penetrating peptide such as a TAT peptide. Typically, the medicament comprises a physiologically acceptable excipient. In some embodiments, the polypeptide consists of SEQ ID NO:1 and a TAT peptide, with the TAT peptide located at the N-terminus of the polypeptide and SEQ ID NO:1 located at the C-terminus of the polypeptide. In some embodiments, the medicament is formulated for injection, such as for intravenous, intramuscular, intraperitoneal, or subcutaneous injection. Or the medicament may be formulated for oral administration. In some embodiments, the medicament further comprises another therapeutic agent effective for treating a poly(GA) disease, for example, antisense oligonucleotides or small molecules (see, e.g., Donnelly et al., *Neuron* 2013 80(2):415-428; Su et al., *Neuron* 2014 85(5):1043-1050). Quite often, the medicament is formulated in a dose form containing an effective amount of the polypeptide for each administration.

In a third aspect, the present invention provides a kit for treating a poly(GA) disease. The kit comprises a container containing a pharmaceutical composition comprising a polypeptide described herein, which is capable of inhibiting expanded GGGGCC-RNA mediated toxicity as verified in an in vitro or in vivo assay. In some embodiments, the kit further comprises a second container containing a second therapeutic agent effective for treating a poly(GA) disease, for example, antisense oligonucleotides or small molecules (see, e.g., Donnelly et al., *Neuron* 2013 80(2):415-428; Su et al., *Neuron* 2014 85(5):1043-1050). In some embodiments, the kit further comprises informational material providing instructions on administration of the pharmaceutical composition.

DEFINITIONS

Figure 1:
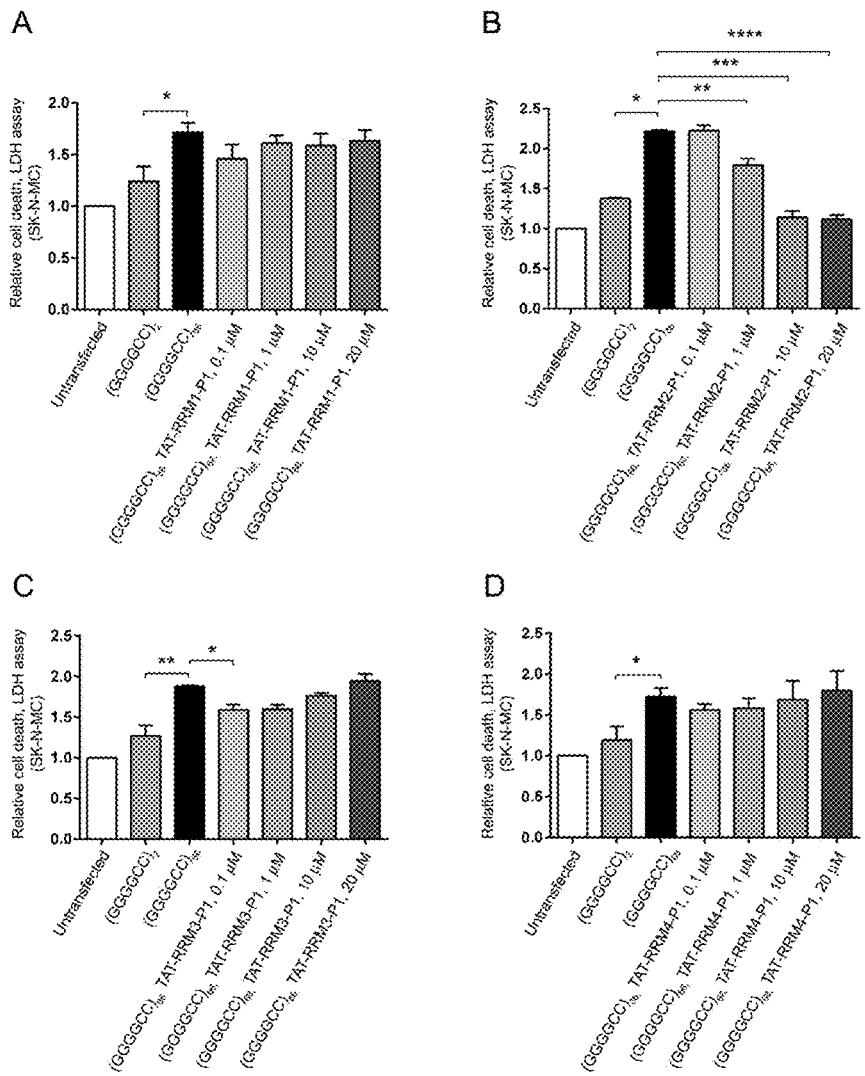
FIG. 1: TAT-RRM2-P1 (TAT-P3L) significantly suppressed $(GGGGCC)_{66}$-induced cell death in SK-N-MC cells. (A) Treatment of TAT-RRM1-P1 didn't alter $(GGGGCC)_{66}$-induced cell death. (B) Treatment of TAT-RRM2-P1 dose-dependently suppressed $(GGGGCC)_{66}$-induced cell death. (C) Low concentration but not high concentration of TAT-RRM3-P1 slightly suppressed $(GGGGCC)_{66}$-induced cell death. (D) Treatment of TAT-RRM4-P1 did not alter $(GGGGCC)_{66}$-induced cell death. $(GGGGCC)_2$ and $(GGGGCC)_{66}$ were expressed by transfection of 1 μg of pAg3-$(GGGGCC)_{2/66}$ plasmid. Various amounts of TAT peptides, 0.1, 1, 10 and 20 μM were then added to individual culture wells. Forty eight hours after treatment, LDH enzyme activity in the cell culture medium was measured. Experimental groups were normalized to the untransfected control. Experiments were repeated for at least 3 times, and data are expressed as mean±S.E.M. * indicates P<0.05,  indicates P<0.01, * indicates P<0.001 and **** indicates P<0.0001.

The term "inhibiting" or "inhibition," as used herein, refers to any detectable negative effect on a target biological process, such as expanded GGGGCC-RNA mediated or Poly(GA)-mediated toxicity. Typically, an inhibition of expanded GGGGCC-RNA mediated or Poly(GA)-mediated toxicity is reflected in a decrease of at least 10%, 20%, 30%, 40%, 50%, 60%, 70%, 80%, 90% or higher, including 100% or complete elimination, of one or more hallmarks of expanded GGGGCC-RNA mediated or Poly(GA)-mediated toxicity as described herein, when compared to a control not given the "inhibition" treatment, such as treatment by administration of small molecule therapeutics described herein. On the other hand, inhibition of expanded GGGGCC-RNA mediated or Poly(GA)-mediated toxicity may also be manifested as increased cell survival, demonstrated in an increase of at least 50%, 60%, 70%, 80%, 90%, 100%, 200%, 300%, 500% or more in the number or length of time of cell survival in the pertinent tissues within the recipient body after the small molecule administration in comparison to a control that has not received the same treatment.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a core amino acid sequence responsible for expanded GGGGCC-RNA binding has at least 80% identity, preferably 85%, 90%, 91%, 92%, 93, 94%, 95%, 96%, 97%, 98%, 99%, or 100% identity, to a reference sequence, e.g., any one of SEQ ID NOs:1-5), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin &

Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used herein, the term "treatment" or "treating" includes both therapeutic and preventative measures taken to address the presence of a disease or condition or the risk of developing such disease or condition at a later time. It encompasses therapeutic or preventive measures for alleviating ongoing symptoms, inhibiting or slowing disease progression, delaying of onset of symptoms, or eliminating or reducing side-effects caused by such disease or condition. A preventive measure in this context and its variations do not require 100% elimination of the occurrence of an event; rather, they refer to an inhibition or reduction in the likelihood or severity of such occurrence or a delay in such occurrence.

A "poly(GA) disease," as used herein, refers to a disease or condition that is associated with, caused by, or exacerbated by, RNA containing an expanded long repeats of GGGGCC trinucleotides (expanded GGGGCC-RNA) and/or poly(GA), poly(GR), poly(PR), poly(PA), or poly(GP) polypeptides, which may be encoded by the expanded GGGGCC-RNA either in sense or antisense direction. Poly (GA) diseases include those diseases, conditions, and symptoms that result from nucleolar stress or endoplasmic reticulum stress caused by expanded GGGGCC-RNA, poly(GA)/(GR)/(PR)/(PA)/(GP) polypeptides, or both. As such, the presence of a poly(GA) disease can be observed at a cellular level by detecting or measuring one or more of the hallmarks of expanded GGGGCC-RNA mediated cytotoxicity or poly (GA)/(GR)/(PR)/(PA)/(GP)-mediated cytotoxicity. Additionally, the presence of a poly(GA) disease can be indicated by the presence of expanded GGGGCC-RNA or poly(GA)/(GR)/(PR)/(PA)/(GP) polypeptides in pertinent cells/tissues of a person being tested for the disease. Furthermore, cells or tissues taken from or present in the body of a patient suffering from poly(GA) disease or suspected to suffer from a poly(GA) disease, e.g., due to hereditary patterns, can exhibit one or more of the hallmarks of expanded GGGGCC-RNA mediated cytotoxicity or poly(GA)/(GR)/(PR)/(PA)/(GP)-mediated cytotoxicity to indicate the presence of a poly(GA) disease, regardless of whether clinical symptoms of the poly(GA) disease are apparent at the time. Exemplary poly(GA) diseases include frontotemporal dementia and amyotrophic lateral sclerosis caused by a hexanucleotide (GGGGCC) repeat expansion in the C9ORF72 gene (c9FTD/ALS). A patient suffering from/diagnosed of a "poly(GA) disease" in this disclosure is distinguished from and is not a patient suffering from/diagnosed of a "polyQ disease" as described in U.S. Ser. No. 15/046,249 and 15/382,380, published as US2017/0233442 and US2017/0181986.

The term "effective amount," as used herein, refers to an amount that produces therapeutic effects for which a substance is administered. The effects include the prevention, correction, or inhibition of progression of the symptoms of a disease/condition and related complications to any detectable extent, e.g., one or more of the hallmarks of expanded GGGGCC-RNA mediated cytotoxicity or poly(GA)-mediated cytotoxicity. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" when used in reference to a given value denotes a range of ±10% of the value.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

"Translocation sequence" or "transduction sequence" refers to a peptide or protein (or active fragment or domain thereof) sequence that directs the movement of a protein from one cellular compartment to another, or from the extracellular space through the cell or plasma membrane into the cell. Examples include the TAT transduction domain (see, e.g., S. Schwarze et al., *Science* 285 (Sep. 3, 1999); penetratins or penetratin peptides (D. Derossi et al., *Trends in Cell Biol.* 8, 84-87); and Herpes simplex virus type 1 VP22 (A. Phelan et al., *Nature Biotech.* 16, 440-443 (1998). Translocation peptides can be fused (e.g. at the amino and/or carboxy terminus), conjugated, or coupled to a polypeptide of the present invention, in order to produce a conjugate compound such as a fusion peptide that may pass into target cells, or through the blood brain barrier and into target cells more easily.

As used herein, the term "nucleolin" or "NCL" refers to the nucleolin protein. Exemplary nucleolin proteins include those of the Chinese Hamster (Genbank Accession No. AAA36966.1), the golden hamster (Genbank Accession No. P08199.2), the Norwegian Rat (Genbank Accession No. EDL75577.1), the house mouse (Genbank Accession No. EDL40222.1), and human nucleolin (Genbank Accession No. EAW70962.1). In some embodiments of this invention, peptides derived from NCL are provided for treatment of expanded GGGGCC-RNA mediated cytotoxicity or poly (GA) disease, e.g., a polypeptide comprising SEQ ID NO:1 but not the full length of NCL protein. In any case, such peptides comprise less than full length (or only partial) NCL sequence. For example, such peptides can be shorter in length, e.g., less than 714 amino acids in length or less than about 25, 30, 35, 40, 45, 50, 55, 60, 65, 70, 75, 80, 85, 90, 95, 100, 110, 120, 125, 130, 140, 150, 175, 200, 225, 250, 275, 300, 350, 400, 500, 600, or 700 amino acids in length. Optionally, one or more heterologous peptide sequences (peptide sequences derived from an origin other than the NCL protein) may be fused to such a partial NCL protein sequence, which may provide an additional length of up to 5, 6, 7, 8, 9, 10, 11, 12, 15, 17, 20, 23, 25, 27, 30, 35, 30, 35, 40, 45, 50, 60, 65, 70, 75, 80, 85, 90, 95, 100, 110, 120, 125, 130, 140, 150, 175, or 200 amino acids.

As used herein, a "polypeptide comprising an NCL RNA recognition motif (RRM) domain" refers to a polypeptide containing a core amino acid sequence that generally corresponds to the amino acid sequence of an RNA recognition motif of nucleolin (NCL). Nucleolin contains three RRM domains, including:

```
RRM1, SEQ ID NO: 3:
F N L F I G N L N P N K S V A E L K V A I S E P F

A K N D L A V V D V R T G T N R K F G Y V D F E S

A E D L E K A L E L T G L K V F G N E I K L E K P

K G;

RRM2, SEQ ID NO: 4:
R T L L A K N L S F N I T E D E L K E V F E D A L

E I R L V S Q D G K S K G I A Y I E F K S E A D A

E K N L E E K Q G A E I D G R S V S L Y Y T G E;
and

RRM3, SEQ ID NO: 5:
K T L V L S N L S Y S A T E E T L Q E V F E K A T

F I K V P Q N Q Q G K S K G Y A F I E F A S F E D

A K E A L N S C N K M E I E G R T I R L E L Q G P
```

These core amino acid sequences may contain some variations such as amino acid deletion, addition, or substitution, but should maintain a substantial level sequence homology (e.g., at least 80%, 85%, 90%, 95%, 98%, or higher sequence homology) to SEQ ID NO:3, SEQ ID NO:4, or SEQ ID NO:5.

Moreover, RRM2 domains, and homologs thereof, are capable of binding RNA containing 1, 2, 3, 4, 5, 10, 15, 20, 25, 30, 35, 40, 50, 60, 75, 100, or more of the GGGGCC hexanucleotide repeats. In addition to this core sequence that is responsible for the polypeptide's ability to bind to expanded GGGGCC-RNA, one or more amino acid sequences of a homologous origin (e.g., additional sequence derived from the same protein, NCL) or a heterologous origin (e.g., an amino acid sequence derived from another unrelated protein) can be included in the polypeptide at the N- and/or C-terminus.

Some examples of the "polypeptide comprising an NCL RRM domain" include SEQ ID NOs:1-5. However, as used herein, a "polypeptide comprising an NCL RRM domain" does not comprise the full length wild-type NCL. For example, in some cases, the "polypeptide comprising an NCL RRM domain (e.g., a polypeptide comprising SEQ ID NO:1)" can be shorter than a full length NCL RRM domain, e.g., less than about 25, 30, 40, 50, 60, 70, 80, 90, 100, 120, 125, 150, 175, or 200 amino acids in length. Optionally, one or more peptides of a heterologous origin, for example, an affinity or epitope tag (such as a GST tag), can be included in the polypeptide at either or both ends to facilitate purification, isolation, or immobilization of the polypeptide. If a heterologous amino acid sequence is included at both ends, each end can be fused to the same heterologous amino acid sequence, or each end can be fused to a different sequence. One example of a polypeptide comprising an NCL RRM domain is a fusion peptide of TAT and SEQ ID NO:1 or 4.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

As used herein, the terms "(GGGGCC)$_n$-mediated toxicity," "expanded GGGGCC-RNA mediated cytotoxicity," and the like refer to cytotoxicity caused by expanded GGGGCC-RNA. Expanded GGGGCC-RNA mediated toxicity can result in nucleolar stress and cell death. Expanded GGGGCC-RNA mediated toxicity can be inferred by detecting or measuring one or more of (i) rRNA upstream control element hypermethylation, (ii) a decrease in rRNA transcription, (iii) a decrease in binding of NCL to the rRNA locus, (iv) an increase in binding between ribosomal proteins and MDM2, (v) stabilization of p53, (vi) accumulation of p53 in the mitochondria, (vii) release of Bcl-xL from Bak, (viii) release of cytochrome c from the mitochondria, (ix) caspase activation, and (x) apoptosis or cell death.

As used herein, the terms "Poly(GA)-mediated cytotoxicity," "Poly(GA)-mediated toxicity," and the like refer to cytotoxicity caused by polypeptides that contain poly di-amino acids GA/GR/PR/PA/GP sequences. Poly(GA)-mediated cytotoxicity can result in cellular stress, endoplasmic reticulum stress, an unfolded protein response, and cell death. Poly(GA)-mediated cytotoxicity can be inferred by detecting or measuring one or more of (i) GRP78/BiP upregulation, (ii) caspase activation, and (iii) apoptosis or cell death. Poly(GA)-mediated cytotoxicity can be observed independently of expanded GGGGCC-RNA mediated cytotoxicity by measuring GRP78/BiP upregulation as explained herein. Similarly, expanded GGGGCC-RNA mediated cytotoxicity can be observed independently of poly(GA)-mediated cytotoxicity by measuring one or more of rRNA hypermethylation, NCL binding to rRNA locus, the level of rRNA expression, and binding between ribosomal proteins and MDM2 as explained herein.

The term "consisting essentially of," when used in the context of describing a composition containing an active ingredient, refers to that the composition does not contain other ingredients possessing any similar or relevant biological activity. For example, a composition consisting essentially of an inhibitor of expanded GGGGCC-RNA mediated or Poly(GA)-mediated toxicity is a compound that does not contain other modulators such as enhancers or inhibitors of expanded GGGGCC-RNA mediated or Poly(GA)-mediated toxicity.

DETAILED DESCRIPTION OF THE INVENTION

I. Introduction

A hexanucleotide repeat expansion in the non-coding region of the C9ORF72 gene causes frontotemporal dementia and amyotrophic lateral sclerosis (c9FTD/ALS). Both the formation of GGGGCC-repeat RNA foci and the expression of repeat-associated translation (RAN) products can induce to nucleolar stress and contribute to C9ORF72-mediated neurodegeneration. As disclosed herein, the present inventors have identified a peptidylic inhibitor, P3L, which is derived from the RNA recognition motif 2 (RRM2) of the nucleolin (NCL) protein and has the amino acid sequence of SEQ ID NO:1 (AEIRLVSKDGKSKGIAYIEFK), can efficiently suppress GGGGCC repeat-associated toxicity in vitro and in vivo. The (GGGGCC)$_{66}$-induced cell death was first confirmed by LDH assay in SK-N-MC cells. Using this model, the inventors showed that the 21-amino acid peptide, P3L, could effectively neutralize GGGGCC repeat-mediated cell death with an empirical IC$_{50}$ value of 103.9±24.6 nM. Through a structure-activity relationship study, Leu5, Ser7, Lys8, Lys13, Gly14, Ile18, Glu19 and Phe20 of TAT-P3L were found to play crucial roles in P3L suppression activity. It was further demonstrated that TAT-P3L could significantly suppress the formation of GGGGCC RNA foci and RAN-mediated poly-GP/R/A protein expression in disease cell model. In addition, it was observed that P3L restored the subcellular localization of both NCL and nucleophosmin (B23) in (GGGGCC)$_{66}$-expensing SK-N-MC cells. The mislocalization of these proteins are markers of nucleolar stress, a pathogenic hallmarks of c9FTD/ALS. Besides in vitro study, it was further showed that feeding the in vivo *Drosophila* GGGGCC pathogenic model with the P3L peptide inhibitor significantly suppressed neurodegeneration, rescued locomotor deficit, and extended lifespan of the animals. Collectively, the present inventors demonstrated for the first time a peptidylic inhibitor could target (GGGGCC)-associated degeneration in c9FTD/ALS. These findings provide a new therapeutic direction for treating c9FTD/ALS.

II. Compositions

A. Inhibitors of (GGGGCC)$_n$-Mediated Toxicity

In some embodiments, compositions are provided that reduce (GGGGCC)$_n$-mediated toxicity in a cell. Reduction of (GGGGCC)$_n$-mediated toxicity can, in some cases, restore rRNA transcription in expanded GGGGCC RNA-expressing cells. For example, synthetic peptides are provided that can bind to or sequester toxic RNA species. In some cases, the synthetic peptides are fragments derived from full-length nucleolin (NCL) but do not encompass the full-length NCL. For example, the synthetic peptides may be derived from an RNA recognition motif (RRM) of full-length nucleolin. In some cases, the synthetic peptides are derived from the RRM2 domain of NCL. The peptides optionally may include one or more additional amino acid sequences from a heterologous origin, i.e., a source other than the NCL protein.

In some cases, compositions for treating (GGGGCC)$_n$-mediated RNA toxicity in a cell include one or more of the above synthetic peptides. Similar peptides have been previously described. For example, compositions for treating (GGGGCC)$_n$-mediated RNA toxicity in a cell can include peptide P3 (amino acid sequence DGKSKGIAYIEFK, SEQ ID NO:2) and/or P3L as well as those described in U.S. Patent Application Publication No. 2014/0357578 and U.S. patent application Ser. No. 15/046,249.

In some cases, the peptides are conservatively substituted at one or more of 1, 2, 3, 4, 5, 6, 7, 8, 9, 10, 11, 12, 13, and 14 positions. The peptides can also be substituted with non-natural amino acids, such as D-amino acids or chemically modified natural amino acids. In some cases, the peptides are truncated. Truncated peptides include peptides in which one or more amino or carboxy terminal residues are removed. In some cases, the peptides are internally deleted such that one or more amino acids that are not at the amino or carboxy terminus are removed. In some cases, the peptides can be modified by the addition of one or more amino acids at the amino or carboxy terminus. For example, a linker or purification tag can be fused to the amino or carboxy terminus. Alternatively, the peptides can be inserted into a scaffold region of a protein, polypeptide, or other molecule as described herein. A scaffold may provide enhanced stability of the peptide in the cell, and may improve binding by reducing the conformational freedom of the peptide or influencing its three-dimensional structure.

B. Production of Peptides that Inhibit (GGGGCC)$_n$-Mediated RNA Toxicity i. General Recombinant Technology Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a nucleolin gene, a polynucleotide encoding a polypeptide comprising the expanded GGGGCC-RNA binding domain RRM2 or a peptide derived therefrom, and synthetic oligonucleotides can be verified after cloning or subcloning using, e.g., the chain termination method for sequencing double-stranded templates of Wallace et al., *Gene* 16: 21-26 (1981).

ii. Coding Sequence for a Polypeptide Comprising an NCL RRM Domain

Polynucleotide sequences encoding nucleolin or its RRM domains have been determined and may be obtained from a commercial supplier or recombinantly produced.

Upon acquiring a nucleic acid sequence encoding a an RNA-recognition motif or encoding a peptide that binds expanded GGGGCC-RNA, the coding sequence can be further modified by a number of well-known techniques such as restriction endonuclease digestion, PCR, and PCR-related methods to generate coding sequences for RRM2-related polypeptides, including RRM mutants and polypeptides comprising an expanded GGGGCC-RNA binding sequence derived from nucleolin. The polynucleotide sequence encoding a desired RRM-related polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding an RRM-related polypeptide. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

iii. Modification of Nucleic Acids for Preferred Codon Usage in a Host Organism

The polynucleotide sequence encoding a polypeptide comprising an NCL RRM can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the RRM-comprising polypeptides.

iv. Chemical Synthesis of a Polypeptide Comprising an NCL RRM Domain

A polypeptide comprising an expanded GGGGCC-RNA binding sequence, e.g., an NCL RRM domain, can also be chemically synthesized using conventional peptide synthesis or other protocols well known in the art.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

B. Expression and Purification of Peptides that Inhibit $(GGGGCC)_n$-Mediated RNA Toxicity Following verification of the coding sequence, a polypeptide comprising an NCL RRM domain of the present invention can be produced using routine techniques in the field of recombinant genetics, relying on the polynucleotide sequences encoding the polypeptide disclosed herein.

i. Expression Systems

To obtain high level expression of a nucleic acid encoding a polypeptide comprising an NCL RRM domain of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli*, *Bacillus sp.*, *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the polypeptide comprising an NCL RRM domain in host cells. A typical expression cassette thus contains a promoter operably linked to the nucleic acid sequence encoding the polypeptide comprising an NCL RRM domain and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Such signal peptides include, among others, the signal peptides from tissue plasminogen activator, insulin, and neuron growth factor. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the RRM-related polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an RRM-related polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

ii. Transfection Methods

Standard transfection methods are used to produce bacterial, mammalian, yeast, insect, or plant cell lines that express large quantities of a polypeptide comprising an NCL RRM domain, which is then purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the RRM-related polypeptide.

iii. Purification of Recombinantly Produced Polypeptides

Once the expression of a recombinant polypeptide comprising an NCL RRM domain in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the polypeptides comprising an NCL RRM domain of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a polypeptide comprising an NCL RRM domain, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., a polypeptide comprising an NCL RRM domain, is expressed in host cells in a soluble form, its purification can follow the standard protein purification procedure described below. This standard purification procedure is also suitable for purifying a polypeptide comprising an NCL RRM domain obtained from chemical synthesis.

(a) Solubility Fractionation

Often as an initial step, and if the protein mixture is complex, an initial salt fractionation can separate many of the unwanted host cell proteins (or proteins derived from the cell culture media) from the recombinant protein of interest, e.g., a polypeptide comprising an NCL RRM domain of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

(b) Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a polypeptide comprising an NCL RRM domain. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

(c) Column Chromatography

The proteins of interest (such as a polypeptide comprising an NCL RRM domain of the present invention) can also be separated from other proteins on the basis of their size, net surface charge, hydrophobicity, or affinity for ligands. In addition, antibodies raised against a segment of nucleolin such as an RNA recognition motif can be conjugated to column matrices and the RRM-related polypeptide immunopurified. All of these methods are well known in the art.

It will be apparent to one of skill that chromatographic techniques can be performed at any scale and using equipment from many different manufacturers (e.g., Pharmacia Biotech).

iv. Verification of Activity

Once a polypeptide comprising an NCL RRM domain is chemically synthesized or recombinantly produced, such as one generally fitting the structural profile described herein, the polypeptide can be then tested to verify its ability to suppress or inhibit cytotoxicity induced by GGGGCC-repeat RNA in an in vitro or in vivo assay, e.g., any one of those known in the pertinent research field or described herein. An effective polypeptide can then be used in a therapeutic scheme for treating a patient suffering from or at risk of developing a poly(GA) disease, such as a human patient who has been diagnosed with a poly(GA) disease or who has a family history of a poly(GA) disease. Use of an effective polypeptide also encompasses the use of the polypeptide for manufacturing a medicament or a kit that is to be used for treating a poly(GA) disease.

III. Methods

A. Identification of Compounds that Inhibit $(GGGGCC)_n$-Mediated RNA Toxicity

An in vitro assay can be used to detect binding between nucleolin and expanded GGGGCC-RNA or detect the binding between a polypeptide comprising an NCL RRM domain and expanded GGGGCC-RNA and to identify compounds that are capable of inhibiting nucleolin: expanded GGGGCC-RNA binding. Such an assay can be performed in the presence of nucleolin or a peptide derived therefrom, such as any one of P3, P3L, or RRM2, and an expanded GGGGCC-RNA, under conditions permitting binding. For convenience, one of the binding partners may be immobilized onto a solid support and/or labeled with a detectable moiety. A third molecule, such as an antibody (which may include a detectable label) to one of the binding partners, can also be used to facilitate detection.

In one embodiment, the expanded GGGGCC-RNA can be labeled with a fluorophore and its intrinsic fluorescence anisotropy due to tumbling in solution can be measured. If a fluorescent molecule is excited with polarized light then the emission will also be polarized. The extent of polarization of the emission is usually described in terms of anisotropy (r). As molecules are tumbling in solution, the emitted light is then depolarized. The depolarization of the fluorescent molecule is dependent on the size and shape of the rotating molecule and also the viscosity of the solution. The smaller the molecule, the more rapidly it rotates and the more the light is depolarized and hence the lower the anisotropy. If a larger molecule interacts with the fluorescent molecule the rotation of the complex will be slower than of the unbound molecules and result in an increase in the fluorescence anisotropy. Inhibitors can be identified by incubating the complex in the presence of a test compound and measuring a reduction in fluorescence anisotropy as compared to a control in which the test compound is not added to the complex.

In some cases, the binding assays can be performed in a cell-free environment; whereas in other cases, the binding assays can be performed in a cell, frequently using cells recombinantly or endogenously expressing an appropriate expanded GGGGCC-RNA molecule. For example, cells expressing an expanded GGGGCC-RNA molecule can be contacted with a test compound and one or more markers of nucleolar stress can be assayed. Such markers include rRNA transcription, rRNA UCE hypermethylation, p53 stability, and apoptosis (e.g., as shown by a decrease in rhabdomeres per ommatidium in the eye of a fruit fly).

To screen for compounds capable of inhibiting nucleolin: expanded GGGGCC-RNA binding, the above-described assays can be performed both in the presence and absence of a test compound, and the level of nucleolin: expanded GGGGCC-RNA binding compared. If nucleolin: expanded GGGGCC-RNA binding is suppressed in the presence of the test compound, for example, at a level of at least 10%, more preferably at least 20%, 30%, 40%, or 50%, or even higher, the test compound is then deemed an inhibitor nucleolin: expanded GGGGCC-RNA binding and may be subject to further testing to confirm its ability to inhibit nucleolar stress.

In some cases, an inhibitor could be identified by detecting an increase in rRNA transcription relative to a control cell expressing an expanded GGGGCC-RNA molecule that is not contacted with the test compound. As another example, an inhibitor could be identified by detecting a decrease in methylation of the rRNA UCE relative to a control cell expressing an expanded GGGGCC-RNA molecule that is not contacted with the test compound. As yet another example, an inhibitor could be identified by detecting a decrease in p53 stabilization (e.g., a reduction in p53 accumulation) relative to a control cell expressing an expanded GGGGCC-RNA molecule that is not contacted with the test compound. As yet another example, an inhibitor could be identified by detecting an increase in the number of rhabdomeres per ommatidium in the eye of a fruit fly relative to a control eye in which the cells express an expanded GGGGCC-RNA molecule that is not contacted with the test compound. More details and some examples of such binding assays can be found in the Examples section of this application.

A binding assay is also useful for confirming that a polypeptide comprising an expanded GGGGCC-RNA binding sequence can indeed specifically bind expanded GGGGCC-RNA. For instance, a polypeptide comprising an RRM2 fragment (e.g., P3 or P3L) but not the full length NCL sequence can be recombinantly expressed, purified, and placed in a binding assay with expanded GGGGCC-RNA, in which every alternate guanine nucleotide is substituted with adenine as a negative control. If deemed to have sufficient expanded GGGGCC-RNA binding ability and specificity, the polypeptide sequence can then be used as a positive control for identifying inhibitors of NCL: expanded GGGGCC-RNA binding. Similarly, a polypeptide comprising a core sequence with a high level of homology (e.g., 90%, 95% or higher) to any one of RRM2 fragment can be tested and, if appropriate, can be used as a positive control for identifying inhibitors of NCL: expanded GGGGCC-RNA binding.

Inhibitors of NCL: expanded GGGGCC-RNA binding can have diverse chemical and structural features. For instance, an inhibitor can be a non-functional NCL mutant that retains expanded GGGGCA-RNA binding ability, an antibody that interferes with NCL: expanded GGGGCC-RNA binding, or any small molecule or macromolecule that simply hinders the interaction between NCL and expanded GGGGCC-RNA. Essentially any chemical compound can be tested as a potential inhibitor of NCL: expanded GGGGCC-RNA binding. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. Methods of Treatment of Poly(GA) Disease

Provided herein are methods for treating poly(GA) disease in a cell that contains an RNA containing a $(GGGGCC)_n$ hexanucleotide repeats. Such methods include contacting the cell with an effective amount of a composition that reduces expanded-GGGGCA RNA-mediated cytotoxicity. Methods of contacting can be performed in vitro and in vivo. In some cases, the RNA containing the $(GGGGCC)_n$ hexanucleotide repeat contains at least 10, 20, 30, 40, 50, 60, 70, 78, or 100 hexanucleotide repeats. Such a cell is likely to exhibit nucleolar stress. In some cases, the composition itself binds the RNA containing the GGGGCC nucleotide repeat. Such binding activity can act to sequester the RNA containing $(GGGGCC)_n$ hexanucleotide repeats from disrupting cellular processes. For example, the composition can sequester the RNA containing GGGGCC hexanucleotide repeats from binding to nucleolin. In some cases, the cell is taken from or present within a subject suffering from a $(GGGGCC)_n$ RNA or poly(GA)-mediated neurodegenerative disease such as c9FTD/ALS.

Methods for treating a poly(GA) disease also include contacting a cell, which expresses an RNA molecule with expanded $(GGGGCC)_n$ hexanucleotide repeats or a peptide containing a poly(GA) amino acid sequence, with an effective amount of a composition that reduces $(GGGGCC)_n$ RNA or poly(GA)-mediated cytotoxicity. In some cases, the composition itself binds the RNA containing the $(GGGGCC)_n$ repeats or the peptide containing the poly(GA) sequence. Such binding activity can act to sequester the $(GGGGCC)_n$ RNA or poly(GA) peptide from disrupting cellular processes. For example, the composition can sequester the poly(GA) peptide from forming intracellular aggregates. In some cases, the cell is taken from or present within a subject suffering from a $(GGGGCC)_n$ RNA or poly(GA)-mediated neurodegenerative disease such as c9FTD/ALS.

IV. Pharmaceutical Compositions and Administration

The present invention also provides pharmaceutical compositions or physiological compositions comprising an effective amount of one or more polypeptides comprising an NCL RRM domain such as P3L and its structurally similar compounds or derivatives including its fusion peptide with a second amino acid sequence of a heterologous origin (e.g., TAT). Use of the compositions can be in both prophylactic and therapeutic applications for the treatment and prevention of a poly(GA) disease. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences,* Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal administration. The preferred routes of administering the pharmaceutical compositions are intravenous or intraperitoneal delivery to a patient in need thereof (e.g., a human patient who is diagnosed of or is at risk of developing a poly(GA) disease) at doses of about 10-100,000 mg, 100-10,000 mg, 50-5,000 mg, 100, 200, 250, or 500 mg of each of the polypeptide for a 70 kg adult human per day or every other day. Some exemplary doses and administration frequencies include about 1, 2, 3, 4, 5, 6, 7, 8, 9, 10, 20, 30, 40, 50, 60, 70, 80, 90, or 100 mg/kg patient body weight for each polypeptide in each administration. Typically one or more polypeptides are administered to the patient either on once per day or per two-day basis. If more than one is administered, they can be administered at the same time or at separate times while all within the same general time frame. The polypeptide therapeutics may be administered in a single pharmaceutical composition or they may be in multiple separate compositions. Similarly, these polypeptides may be administered at the same time, or they may be administered on different days but all in close proximity to each other's administration, e.g., one administered on day 1 and other or others administered on day 2, such that the combined effects of these small molecules being co-administered are obtained. The appropriate dose may be administered in a single daily/bi-daily (once every other day) dose or as divided doses presented at appropriate intervals, for example as two, three, four, or more subdoses per day, or one dose every two, three, four, or five days.

For preparing pharmaceutical compositions of this invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., P3L and/or its derivatives. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient (e.g., P3L and/or its derivatives). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active component of a polypeptide comprising an NCL RRM domain such as P3L and/or its derivatives with encapsulating material as a carrier providing a capsule in which the small molecule (with or without other carriers) is surrounded by the carrier, such that the carrier is thus in association with the small molecule or the active component. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., P3L and/or its derivatives) or sterile solutions of the active component in solvents comprising water, buffered water, saline, PBS, ethanol, or propylene glycol are examples of liquid compositions suitable for parenteral administration including subcutaneous, intramuscular, intravenous, or intraperitoneal administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., P3L and/or its derivatives) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between about 3 and about 11, more preferably from about 5 to about 9, and most preferably from about 7 to about 8.

The pharmaceutical compositions one or more polypeptides comprising an NCL RRM domain such as P3L and/or its derivatives can be administered to a patient who have received a diagnosis of a poly(GA) disease or is at risk of developing such a disease at a later time in an amount sufficient to prevent, eliminate, reverse, or at least partially slow or arrest the symptoms of poly(GA) disease such as any of the clinical symptoms of the cytotoxicity related to, caused by, or enhanced by expanded GGGGCC-repeat RNA or poly(GA) polypeptide. An amount adequate to accomplish this goal is defined as a "therapeutically effective dose." Amounts effective for this use will depend on the (expected) severity of the condition, route of administration, frequency of administration, and the body weight and general physical state of the patient, but generally range from about 1 mg to about 1000 mg per kg patient body weight, or about 5-500 mg/kg, about 10-100 mg/kg, about 20-50 mg/kg, e.g., about 10, 20, 25, 30, 40, 50, or 80, 100, 150, 200, or 300 mg/kg body weight for each small molecule therapeutic agent in each administration.

Single or multiple administrations of the compositions can be carried out with dose levels and pattern being selected by the treating physician. In any event, the pharmaceutical formulations should provide a quantity of a polypeptide comprising an NCL RRM domain such as P3L and/or its derivatives sufficient to effectively inhibit the undesired symptoms in the patient relating to expanded GGGGCC-repeat RNA or poly(GA) polypeptide mediated cytotoxicity. Typically, the administration lasts at least 1, 2, 3, 4, 6, 8, 10, or 12 weeks and for as long as needed such as 6 months, 1, 2, 3, 4, 5, or 10, 15, 20 years on a daily, twice a day, bi-daily (once every other day), or weekly schedule.

While other active ingredient are generally not necessary to be co-administered to a recipient with the polypeptide therapeutics such as P3L and/or its derivatives in order to treat a patient suffering from or at risk of poly(GA) disease, it is optional that one or more additional therapeutically effective compounds may be co-administered along with the polypeptide(s), either in the same pharmaceutical composition(s) with the polypeptide(s) or in a separate pharmaceutical composition. For description of other therapeutic ingredients, see, e.g., U.S. Patent Application Publication No. 2014/0357578; Donnelly et al., *Neuron* 2013 80(2):415-428; and Su et al., *Neuron* 2014 85(5):1043-1050.

V. Kits

The invention also provides kits for treating a poly(GA) disease according to the method of the present invention. The kits typically include a first container that contains a pharmaceutical composition comprising a polypeptide comprising an NCL RRM domain that is therapeutically effective to ameliorate the symptoms of a poly(GA) disease, such as P3L or any one of its derivatives possessing a similar biological activity (e.g., capable of inhibiting cytotoxicity induced by expanded GGGGCC-repeat RNA), optionally with an additional container that contains a pharmaceutical composition comprising another therapeutically effective compound for ameliorating the symptoms of a poly(GA) disease, such as another different polypeptide or polynucleotide or small molecule therapeutic agent known to be effective for inhibiting cytoxicity mediated by expanded GGGGCC-repeat RNA or poly(GA) protein. For example, Donnelly et al., Neuron 2013 80(2):415-428, and Su et al., Neuron 2014 85(5):1043-1050, describe antisense oligonucleotides and small molecules that are potentially effective for treating neurotoxicity in c9FTD/ALS. In some variations of the kits, a single container may contain a pharmaceutical composition comprising two or more of compounds effective for treating a poly(GA) disease such as polypeptide P3L and its derivatives. The kits may further include informational material providing instructions on how to dispense the pharmaceutical composition(s), including description of the type of patients who may be treated (e.g., human patients who have received a diagnosis of a poly(GA) disease or have been deemed as risk of developing a poly(GA) disease, e.g., due to a strong propensity indicated by family history), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Introduction

Amyotrophic lateral sclerosis (ALS) and frontotemporal dementia (FTD) are rare and incurable neurodegenerative disorders[1,2]. A GGGGCC hexanucleotide repeat expansion (HER) in non-coding region of C9orf72 is a major genetic cause of both FTD and ALS (c9FTD/ALS)[1,3]. In healthy individuals, this hexanucleotide repeat is fewer than 33 repeats. In c9FTD/ALS patients, this hexanucleotide repeat tract is expanded to 400-4400 repeats[1,4,5]. Over the past decade, several pathogenic mechanisms, such as recruitment of RNA binding protein by GGGGCC RNA foci[6-8] and repeat-associated non-ATG translation (RAN)[9,10], have been proposed to explain how C9orf72 mutations cause neurodegeneration.

Pathogenic RNA transcribed from expanded GGGGCC-containing C9orf72 was reported to form intracellular RNA foci[1]. Biochemical and microscopic investigations showed that C9orf72 RNA foci are capable of recruiting RNA binding proteins and splicing factors[7,8,11]. The direct interaction of the nucleolar protein nucleolin (NCL) with GGGGCC RNA G-quadruplexes was observed[7]. Nucleolin was shown to become more diffusely localized outside the nucleolar region in cells expressing expanded GGGGCC C9orf72 RNA and in patients[7]. More importantly, a decrease in the processing of the precursor 45S rRNA into the mature cleaved 28S, 18S and 5.8S rRNAs in C9orf72 HRE patient B lymphocytes was reported[7]. Experimental evidence thus support that expanded GGGGCC repeat transcripts cause dysfunction of NCL which subsequently induces nucleolar stress in c9ALS-FTD.

Although the GGGGCC-repeat expansion is located in non-coding region between exons 1a and 1b of C9orf72[1,12], Mori et al showed that GGGGCC repeat are transcribed and translated bi-directionally[13]. More recently, both the sense and anti-sense GGGGCC C9orf72 transcripts were reported to generate different dipeptide repeat (DPR)-containing proteins that are composed of GA, GP, GR, PR and AP dipeptide repeats[14] via the RAN translation mechanism[15]. Among five RAN translation products, poly-GR and poly-PR were reported to contribute to GGGGCC repeat-mediated neurotoxicity both in both cell[9] and Drosophila models[10]. Interestingly, the non-RAN-mediated expression of poly-GR/-PR using non-repeat codon also caused a mislocalization of NCL protein and a reduction of rRNA maturation in cells[9], suggesting DPR products by per se can induce nucleolar stress.

Nucleolar stress is a cellular response to the failure in ribosome biogenesis and/or ribosome malfunction[16]. A reduction in ribosomal RNA (rRNA) transcription causes an imbalance in the intracellular levels of ribosomal RNAs and ribosomal proteins, which subsequently triggers ribosome assembly defects and eventually leads to nucleolar stress-induced apoptosis[17,18] Nucleolar stress response has been implicated in the pathogenesis of various neurodegenerative diseases[19], including Alzheimer's, Parkinson's Diseases, polyglutamine (polyQ) diseases, as well as c9ALS-FTD. The inventors' previous work demonstrated out a peptidylic inhibitor, P3, derived from RRM2 of NCL protein, could specifically inhibited expanded CAG repeat-mediated nucleolar stress and subsequently neurodegeneration in polyQ disease[20]. This prompts efforts to develop a peptidylic inhibitor from RRM of NCL protein to target GGGGCC repeat-mediated nucleolar stress and eventually inhibit neurodegeneration in c9ALS-FTD.

Results

According to the information available on the structure of the RNA-recognition motifs (RRMs) of the NCL protein (PDB ID=2KRR)[21], and the RRM/RNA binding interface[22], we designed four peptides (RRM1-P1, RRM2-P1, RRM3-P1 and RRM4-P1) and each of which covered a particular NCL RRM (Table 1). The TAT peptide is a cell-penetrating peptides (CPP) derived from the HIV-1 virus transactivator of transcription protein, which has been reported to mediate the translocation of proteins across the cell membrane[23,24]. TAT fusion peptides (TAT-RRM1-P1, TAT-RRM2-P1, TAT-RRM3-P1 and TAT-RRM4-P1)[25,26] were synthesized and tested for their abilities on suppressing (GGGGCC)$_{66}$-induced toxicity.

TABLE 1

| Peptides | Sequences | Derived from |
|---|---|---|
| TAT | YGRKKRRQRRR (SEQ ID NO: 6) | HIV-1 virus transactivator |
| TAT-RRM1-P1 | YGRKKRRQRRRTGTNRKFGYVD (SEQ ID NO: 7) | RRM1 of NCL |
| TAT-RRM2-P1 (TAT-P3L) | YGRKKRRQRRRAEIRLVSKDGK SKGIAYIEFK (SEQ ID NO: 8) | RRM2 of NCL |
| TAT-RRM3-P1 | YGRKKRRQRRRTFIKVPQNQNG KSKGYAF (SEQ ID NO: 9) | RRM3 of NCL |
| TAT-RRM4-P1 | YGRKKRRQRRRRARIVTDRETG SSKGFGFVD (SEQ ID NO: 10) | RRM4 of NCL |

By means of the lactate dehydrogenase (LDH) cytotoxicity assay[27], it was demonstrated that the expression of expanded $(GGGGCC)_{66}$ caused significant cell death when compared with expression of the control construct $(GGGGCC)_2$. Treatment of TAT-RRM1-P1 and TAT-RRM4-P1 did not demonstrate any modifying effect on $(GGGGCC)_{66}$ toxicity in SK-N-MC cells (FIGS. 1A, 1B & 1D). At low concentration, TAT-RRM3-P1 slightly inhibited cell death (FIG. 1C). However, this peptide by itself elicited cytotoxicity when the dose was raised increased (FIG. 1D). Peptide TAT-RRM2-P1 was discovered as being capable of dose-dependently suppression of $(GGGGCC)_{66}$-induced cell death in SK-N-MC cells (FIG. 1B). Based on these results, the inventors decided to focus their investigations on TAT-RRM2-P1 and re-named this peptide as TAT-P3L.

Figure 2:
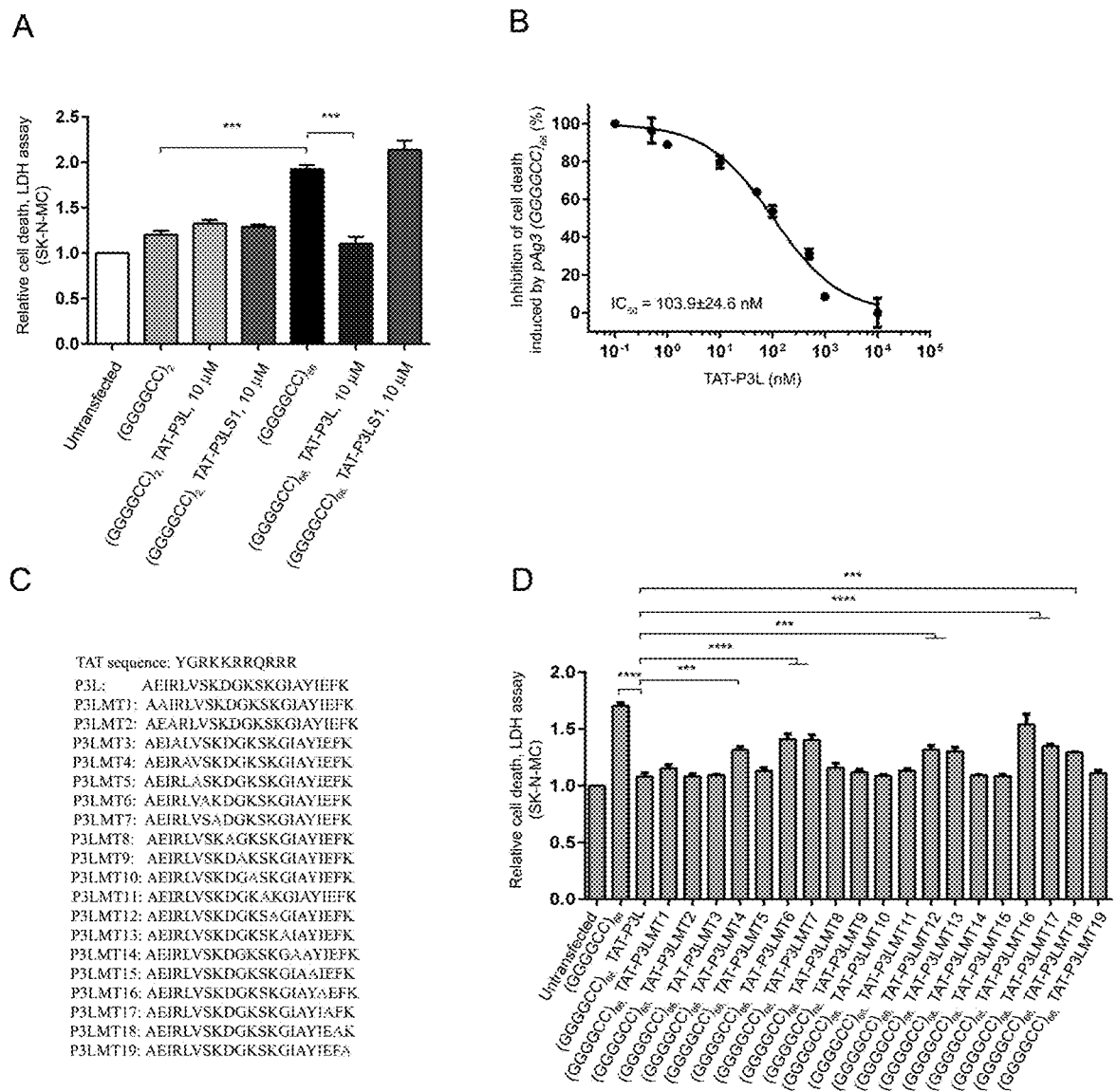
FIG. 2: Calculated maximal inhibitory concentration ($IC_{50}$) detection and structural-activity relationship study of TAT-P3L. (A) TAT-P3L is not cytotoxic and can suppress $(GGGGCC)_{66}$-induced cell death. The treatment of the non-toxic $(GGGGCC)_2$-expressing control cells with TAT-P3L did not elicit any cytotoxicity. The treatment of $(GGGGCC)_{66}$-expressing cells with TAT-P3L significantly suppressed cell death, whereas the control scrambled peptide, TAT-P3LS1, showed no effect on inhibiting $(GGGGCC)_{66}$-induced cell death. (B) $IC_{50}$ of TAT-P3L on inhibition of $(GGGGCC)_{66}$-induced cell death. The $IC_{50}$ value represents the concentration of TAT-P3L that reduced LDH enzyme activity by 50% when compared with the untreated control group. (C) Sequences of TAT and P3L mutants. TAT peptide was attached to the N terminus of each mutants (TAT=SEQ ID NO:6; PL3=SEQ ID NO:1; mutants PL3MT=SEQ ID NO:14 (PL3MT1) to SEQ ID NO:32 (PL3MT19), respectively). (D) Structure-activity relationship study of TAT-P3L. $(GGGGCC)_2$ and $(GGGGCC)_{66}$ were expressed by transfection of 1 μg of pAg3-$(GGGGCC)_{2/66}$ plasmid. Ten micromolar of respective peptide was then added to individual culture wells. Forty eight hours after treatment, LDH enzyme activity in the cell culture medium was measured. Experimental groups were normalized to the untransfected control. Experiments were repeated for at least 3 times, and data are expressed as mean±S.E.M. * indicates P<0.001 and ** indicates P<0.0001.

Using LDH assay, treatment of 10 μM of TAT-P3L did not elicit any observed cytotoxicity in unexpanded $(GGGGCC)_2$-expressing cells (FIG. 2A), and the calculated maximal inhibitory concentration ($IC_{50}$) of TAT-P3L in suppressing expanded $(GGGGCC)_{66}$-induced cell death is 103.9±24.6 nM (FIG. 2B). Thus, TAT-P3L is therefore considered as an effective and non-toxic peptidylic inhibitor candidate for c9ALS-FTD (FIG. 2A). We next designed a scrambled peptide, TAT-P3LS1, which carries the same amino acid composition as TAT-P3L but displays a different predicted secondary structure of TAT-P3L. The TAT-P3LS1 peptide showed no effect on inhibiting cell death in disease cell model (FIG. 2A), and this peptide served as a negative control in subsequent investigations.

In order to improve the efficacy of P3L, a structure-activity relationship study was performed to determine the crucial amino acid residues of TAT-P3L for inhibiting $(GGGGCC)_{66}$-induced cell death. Nineteen TAT-P3L mutants, each of which carries a single alanine substitution, were synthesized (FIG. 2C). Mutants that demonstrated the same suppression effect as the P3L peptide reflect that these positions are not essential for P3L bioactivity, thus they are tolerable to alanine substitution. These mutants include TAT-P3LMT1/2/3/4/8/9/10/11/14/15/19 (FIG. 2D). In contrast, the bioactivity of mutants TAT-P3LMT4/6/7/12/13/16/17/18 significant deviated from the P3L (FIG. 2D). Based on this observation, Leu5, Ser7, Lys8, Lys13, Gly14, Ile18, Glu19 and Phe20 of P3L are predicted to play pivotal roles in mediating the suppression effect of $(GGGGCC)_{66}$ toxicity.

Figure 3:
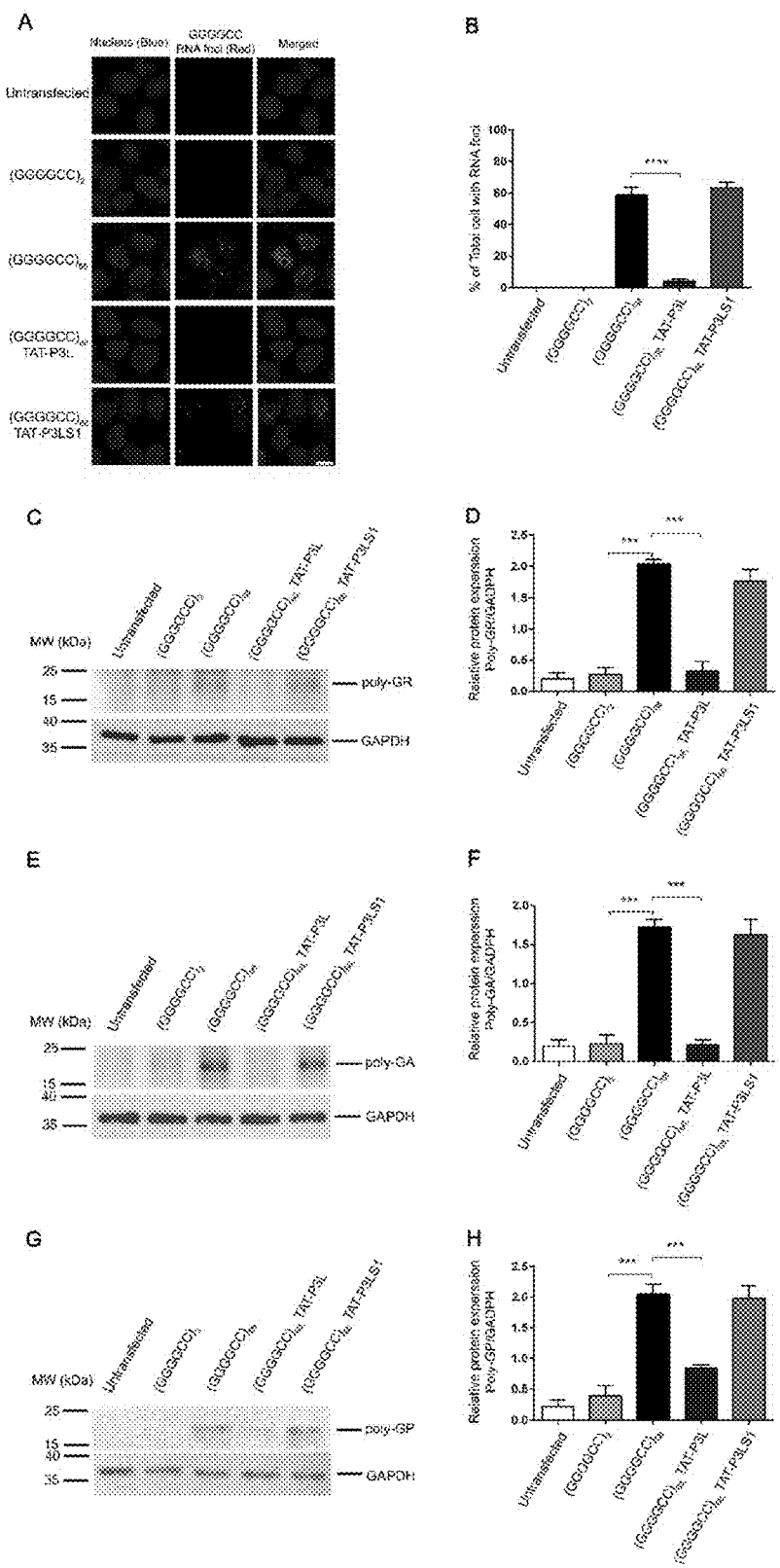
FIG. 3: Treatment of TAT-P3L suppressed GGGGCC RNA foci formation and RAN translation in $(GGGGCC)_{66}$-expressing SK-N-MC cells. (A) Treatment of TAT-P3L suppressed GGGGCC RNA foci formation in $(GGGGCC)_{66}$-expressing SK-N-MC cells. In situ hybridization was performed to detect GGGGCC RNA foci (red) using a TYE563-labeled LNA probe. Nuclei (blue) was stained by Hoechst 33332. Scale bar represents 10 μm. (B) Quantification of the number of SK-N-MC cells containing RNA foci after transfection. (C) Treatment of TAT-P3L suppressed poly-GR protein expression in $(GGGGCC)_{66}$-expressing SK-N-MC cells. (D) Statistical analysis of band intensity (poly-GR/GAPDH) of (C). (E) Treatment of TAT-P3L suppressed poly-GA protein expression in $(GGGGCC)_{66}$-expressing SK-N-MC cells. (F) Statistical analysis of band intensity (poly-GA/GAPDH) of (E). (G) Treatment of TAT-P3L suppressed poly-GP protein expression in $(GGGGCC)_{66}$-expressing SK-N-MC cells. (H) Statistical analysis of band intensity (poly-GR/GAPDH) of (G). $(GGGGCC)_2$ and $(GGGGCC)_{66}$ were expressed by transfection of 1 μg of pAg3-$(GGGGCC)_{2/66}$ plasmid. Ten micromolar of respective peptide was then added to individual culture wells. Forty eight hours after treatment, cells were collected and lysed for western blotting detection. GAPDH was used as loading control. Only representative blots are shown. All experiments were repeated for at least 3 times with consistent results obtained. Data are expressed as mean±S.E.M. and *** indicates P<0.001.

As mentioned above, both the formation of GGGGCC RNA foci and expression of RAN translation products contribute to the pathogenesis of c9ALS-FTD[7,9,13]. It was next investigated if treatment of TAT-P3L can alter GGGGCC RNA foci formation and RAN translation. Using a TYE563 labeled $(GGGGCC)_{2.5}$ LNA probe[28], the formation of intracellular GGGGCC RNA foci in $(GGGGCC)_{66}$-expressing SK-N-MC cells was first confirmed by in situ hybridization (FIG. 3A). No RNA foci-like structure was observed in untransfected control or $(GGGGCC)_2$-expressing cells, indicating the LNA probe used could specifically detect GGGGCC RNA foci in the disease cell model (FIGS. 3A & B). Using this model, it was found that the treatment of TAT-P3L but not TAT-P3LS1 significantly decreased the number of cells that formed intracellular GGGGCC RNA foci (FIGS. 3A & B). It was also shown that no RNA foci-like structure formed in TAT-P3L or TAT-P3LS1-treated cells in control group. This indicates that the TAT-P3L/TAT-P3LS1 treatment per se would not induce foci formation.

The dipeptide repeat (DPR) proteins translated from the expanded GGGGCC RNA include poly-GR, poly-GA and poly-GP proteins[28]. All these three DPR proteins expression was observed in our $(GGGGCC)_{66}$ cell model, but not in $(GGGGCC)_2$ control nor untransfected cells (FIGS. 3C, E and G). This confirms that the antibodies used in the analysis could specifically detect poly-GR, poly-GA and poly-GP RAN translated from $(GGGGCC)_{66}$ RNA. Using these antibodies, it was demonstrated that the treatment of $(GGGGCC)_{66}$-expressing cells with TAT-P3L, but not TAT-P3LS1, significantly suppressed poly-GR, poly-GA and poly-GP protein expression (FIG. 3C-H). This indicates P3L can effectively inhibit RAN translation from $(GGGGCC)_{66}$ RNA.

Figure 4:
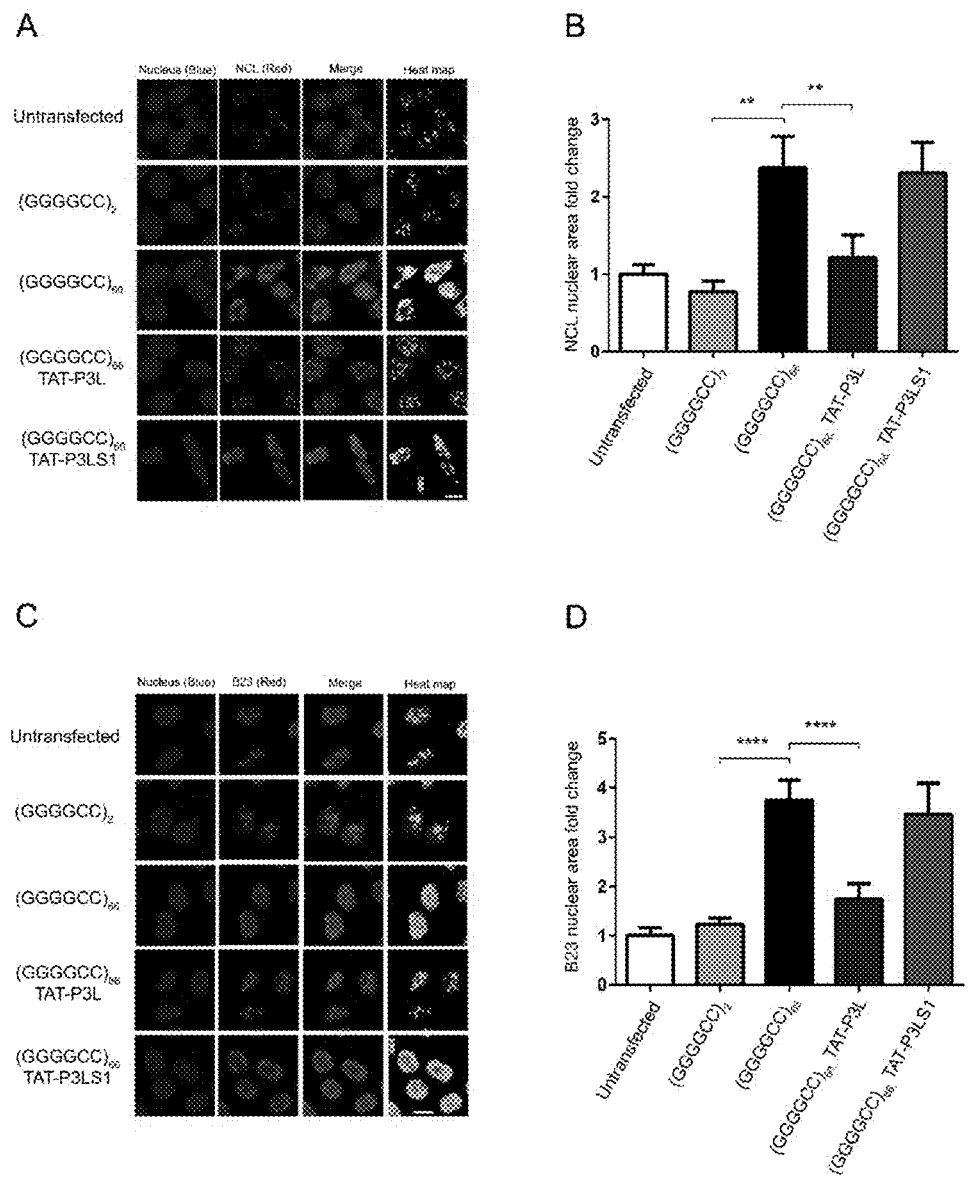
FIG. 4: Treatment of TAT-P3L suppressed nucleolar stress in $(GGGGCC)_{66}$-expressing SK-N-MC cells. (A) TAT-P3L inhibited the mislocalization of NCL protein in $(GGGGCC)_{66}$-expressing cells. (B) Statistical analysis of nuclear NCL fold change of (A). (C) TAT-P3L inhibited the translocation of B23 protein from nucleolus to nucleoplasm in $(GGGGCC)_{66}$-expressing cells. (D) Statistical analysis of nuclear B23 fold change of (C). $(GGGGCC)_2$ and $(GGGGCC)_{66}$ were expressed by transfection of 1 μg of pAg3-$(GGGGCC)_{2/66}$ plasmid. Ten micromolar of respective peptide was then added to individual culture wells. Forty eight hours after treatment, the cells were subjected to immunofluorescence using anti-NCL or anti-B23 antibody (red). Nuclei were stained with Hoechst 33343 (blue). A heat map of NCL intensities marks the difference between cells. The scale bars indicate 10 μm. The pixel area of NCL relative to the area of the nucleus were calculated and normalized to untransfected control. All experiments were repeated for at least 3 times with consistent results obtained. n=150-300 cells were measured for each condition. Data are expressed as mean±S.E.M.  indicates P<0.01 and ** indicates P<0.0001.

As mentioned above, both GGGGCC RNA foci and poly-GR/-PR DPR proteins induce nucleolar stress in C9orf72 HIRE-linked samples[7,9]. The subcellular localization of NCL and nucleophosmin (B23) are regarded as markers of nucleolar stress[29,30]. Confocal images showed that endogenous NCL and B23 proteins were confined to the nucleolus in control cells (FIGS. 4A & C). In contrast, NCL was found to be more dispersed throughout the nucleus and B23 was translocated from the nucleolus to the nucleoplasm in $(GGGGCC)_{66}$-expressing cells, as shown in heat maps indicating the density (FIGS. 4A & C). The observation of such alteration of subcellular localization suggests an induction of nucleolar stress in this disease cell model. Using this model, we demonstrated that cells treated with TAT-P3L restored the normal subcellular localization of NCL and B23 in $(GGGGCC)_{66}$-expressing cells, highlighting the suppression effect of TAT-P3L on nucleolar stress in our disease cell model.

Figure 5:
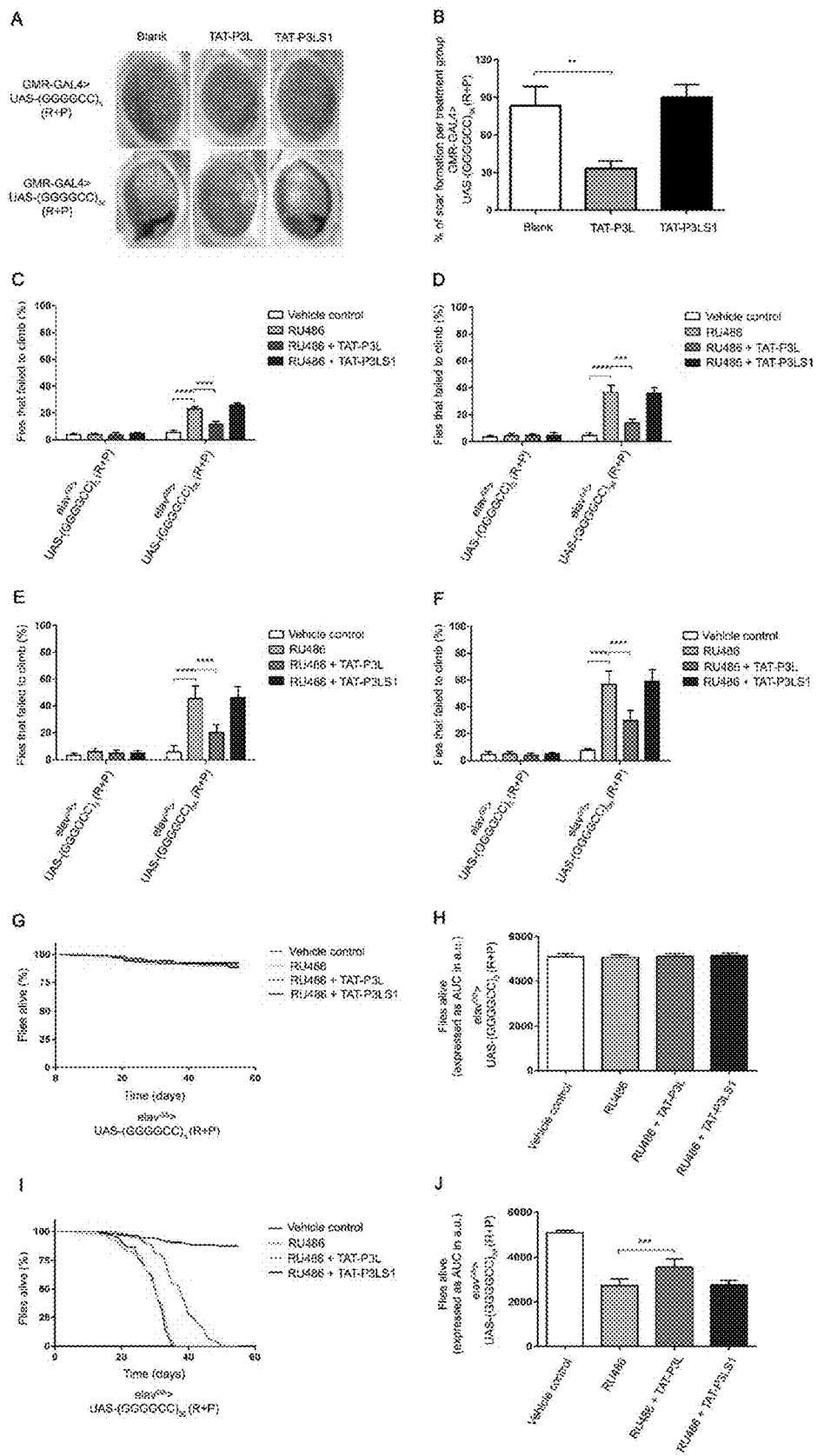
FIG. 5: Treatment of TAT-P3L inhibited eye degeneration, delayed climbing defect and extended lifespan of UAS-(GGGGCC)$_{36}$ flies. (A) Treatment of TAT-P3L inhibited eye degeneration of UAS-(GGGGCC)$_{36}$ flies (express both GGGGCC RNA and DPR proteins). For External eye assay, flies were treated with 100 μM of TAT-P3L or TAT-P3LS1. Images was captured on 1 day-old adult flies. Genotype were: w; GMR-Gal4/UAS-(GGGGCC)$_3$ and w; GMR-Gal4/UAS-(GGGGCC)$_{36}$. Experiments were repeated for 3 times, and at least 30 fly eyes were captured and calculated. (B) Statistical analysis of scar formation of (A). (C-F) Treatment of TAT-P3L rescued the climbing defect of UAS-(GGGGCC)$_{36}$ flies at 10, 15, 20 and 25 days post eclosion (dpe). (G) Treatment of TAT-P3L did not alter the lifespan of UAS-(GGGGCC)$_3$ flies. (H) Statistical analysis of (G). (I) Treatment of TAT-P3L extended lifespan of UAS-(GGGGCC)$_{36}$ flies. (J) Statistical analysis of (I). For climbing ability and lifespan assay, flies of 2dpe were feed with food containing different drug combination including vehicle control (ethanol), Mifepristone (RU486, 200 μM), RU486 (200 μM) plus TAT-P3L (50 μM), and RU486 (200 μM) plus TAT-P3LS1 (50 μM). Mifepristone (RU486, 200 μM) was used to induce transgene expression. The climbing ability assay was repeated for 6 times, and at least total 90 flies per treatment were scored. The lifespan assay was repeated for at least 6 time and total over 100 flies per treatment were recorded. Genotype of (C-I) were: w; UAS-(GGGGCC)$_3$/+; elav$^{GS}$/+ and w; UAS-(GGGGCC)$_{36}$/+; elav$^{GS}$/+. Mifepristone (RU486, 200 μM) was used to induce transgene expression. Data are expressed as mean±S.E.M. * indicates P<0.001 and ** indicates P<0.0001.

Besides in vitro study, we also investigated the effect of TAT-P3L on inhibiting neurodegeneration in an UAS-$(GGGGCC)_{36}$ fly model[10], one of the in vivo models that expresses both GGGGCC repeat RNA and DPR proteins. It has been reported that expression of UAS-$(GGGGCC)_{36}$ via the GMR-GAL4 driver caused severe eye defect using external eye assay[10]. Using the same assay, it was demonstrated that treatment of TAT-P3L but not TAT-P3LS1 significantly inhibited the scar formation in eye, demonstrating the suppression effect of P3L on eye degeneration (FIGS. 5A & B). Furthermore, the treatment of TAT-P3L did not cause any observable eye defect in control UAS-$(GGGGCC)_3$ fly model (FIGS. 5A & B), indicating TAT-P3L treatment is not toxic in vivo.

In addition to external eye assay, climbing ability and lifespan assay were also reported to be effective tools for evaluating new therapeutic drugs for neurodegenerative diseases[31]. The inventors first confirmed that flies expressing UAS-$(GGGGCC)_{36}$ globally in neurons using elav-GeneSwitch (elav$^{GS}$) driver induced progressive loss of climbing ability and lethality when compared to control UAS-$(GGGGCC)_3$ flies (FIG. 5C-J). Using the climbing ability assay, it was found that the treatment of TAT-P3L significantly rescued the climbing defect of UAS-$(GGGGCC)_{36}$ flies at all time points examined (FIG. 5C-F). Further, P3L treatment per se was not found to be affecting the climbing ability of control flies (FIG. 5C-F). Using lifespan assay, we found that treatment of TAT-P3L did not alter the lifespan of control UAS-$(GGGGCC)_3$ flies (FIGS. G&H). Most importantly, it was observed that the lifespan of UAS-$(GGGGCC)_{36}$ disease flies was extended from about 35 days (untreated) to about 50 days (treated).

Materials and Methods
Synthesis of Peptides

All peptides were purchased from GenScript USA Inc. The sequences of TAT peptide, TAT-RRM1-P1, TAT-RRM2-P1(TAT-P3L), TAT-RRM3-P1 and TAT-RRM4-P1 are shown in Table 1. The sequences of nineteen TAT-P3L mutants are shown in FIG. 2C. Amino acid sequence of P3LS1 used in this study was GGEDIKSRVEAASILY-FIKKK (SEQ ID NO: 11) and the TAT CPP peptide was attached at the N terminus of P3LS1. The purity of peptides used in cell experiments was over 90%. Desalted peptides were used in *Drosophila* feeding assays.

Cell Culture, Plasmid Construction, Plasmid Transfection and Peptide Treatment

SK-N-MC cells were kindly provided by Prof. Dobrila D. Rudnicki (Johns Hopkins University, USA). They were cultured at 37° C. with 5% $CO_2$ in DMEM supplemented with 10% FBS and 1% penicillin-streptomycin. The pAg3-$(GGGGCC)_{2/66}$ plasmids were kindly provided by Prof. Leonard Petrucelli (Mayo Clinic, USA). Transient transfection of 1 μg of pAg3-$(GGGGCC)_{2/66}$ to SK-N-MC cells was performed using Lipofectamine 2000 (Thermo Fisher Scientific). Ten micromolar of respective peptide was added into culture well immediately after transfection unless otherwise stated.

Lactate Dehydrogenase (LDH) Cytotoxicity Assay and $IC_{50}$ Determination

SK-N-MC cells were seeded on a 24-well plate at a density of $0.8 \times 10^5$, and pAg3-$(GGGGCC)_{2/66}$ construct were used to transfect the cells. Lactate dehydrogenase enzyme activity in the cell culture medium was measured 48 h post drugs treatment using the Cytotox 96 non-radioactive cytotoxicity assay (Promega).

For $IC_{50}$ detection, various amount of TAT-P3L, 0.1, 0.5, 1, 10, 50, 100, 500, 1,000 and 10,000 nM were added to individual culture wells after transfection. Forty eight hours after treatment, LDH enzyme activity in the cell culture medium was measured as described before. Experimental groups were normalized to the untransfected control. After normalization, data were analyzed using the dose response-inhibition curve (nonlinear regression-variable slope) to determine the $IC_{50}$ value (Prism6 software, GraphPad Software, Inc.).

RNA Fluorescence In Situ Hybridization of Cultured Cells Expressing $(CCCCGG)_n$ Expression Vectors In situ hybridization was carried out to evaluate the effect of TAT-P3L on GGGGCC RNA foci formation in $(CCCCGG)_{2/66}$-expressing SK-N-MC cells. In brief, $0.8 \times 10^5$ SK-N-MC cells were seeded and grown on glass coverslips in 24-well plate. Ten micromolar of TAT-P3L or TAT-P3LS1 were added immediately after transfection of 1 μg of pAg3-$(GGGGCC)_{2/66}$ plasmid. After 48 h, cells were fixed with 4% paraformaldehyde for 10 min and permeabilized with 0.5% Triton-X 100 for 5 min at room temperature. Cells were then washed with phosphate buffered saline treated with diethylpyrocarbonate (DEP-CPBS) three times, and hybridized with 40 nM denatured TYE563-labeled LNA probe (5'-TYE563-CCCGGCCCCGGCCCC-3'; SEQ ID NO:13; Exiqon, Inc) in hybridization buffer (50% formamide, 10% dextran sulfate, 2× saline-sodium citrate buffer (SSC), 50 mM sodium phosphate buffer) 6 h at 65° C. After washing once with 0.1% Tween-20/2×SSC for 5 min at room temperature, cell were further washed with 0.1×SSC 3 times at 65° C. for 10 min. Nuclei were counterstained with Hoechst 33342 (1 μg/ml, Thermo Fisher Scientific) prior to mounting coverslips. Images were obtained on an OLYMPUS FV1000 IX81-TIRF confocal microscope.

Immunostaining

SK-N-MC cells were seeded and grown on glass coverslips at a density of $0.8 \times 10^5$ in 24-well plate. Forty eight hours after treatment, cells were fixed with 4% paraformaldehyde followed by three times wash with 1×PBS. Cells were then permeabilized in 0.5% Triton X-100 for 10 min at room temperature followed by three washes with 1×PBS. After washing step, cells were blocked with 5% BSA in 1×PBS for 1 h at room temperature. The NCL (1:500, Abcam) or B23 (1:500, Abcam) antibody was then applied with 5% BSA (1:500) 2 h at room temperature. Once the primary antibody was removed, Cells were washed three times with 1×PBS and incubated with an anti-rabbit Cy3 or an anti-mouse Cy3 secondary antibody (1:400, Jackson Labs) 1 h at room temperature. After washing with 1×PBS, nuclei were counterstained with Hoechst 33342 (1 μg/ml, Thermo Fisher Scientific) prior to mounting coverslips. Images were obtained on an OLYMPUS FV1000 IX81-TIRF confocal microscope. A single focal plan was obtained through the centre of the nucleus. The method of quantification of NCL and B23 nuclear area fold change was described previously[7]. In order to quantify both dispersed NCL and dense nucleolar NCL, a threshold setting in ImageJ ranging from 25-100 was used to measure the pixel area of NCL relative to the area of the nucleus outlined by the Hoechst staining. Over 150 cells were measure per treatment and data were normalized to untransfected control.

Western Blotting

All protein samples were resolved on 15% SDS-PAGE, and detected using the following antibodies: anti-C9orf72 poly (GR) (Cosmo Bio Co.; 1:1,000) for poly-GR proteins, anti-C9orf72 poly (GA) (Cosmo Bio Co.; 1:1,000) for poly-GA proteins and anti-C9orf72 poly (GP) (Cosmo Bio Co.; 1:1,000) for poly-GP proteins. GAPDH was detected by 6C5 (Thermo Fisher Scientific; 1:2,000). Each experiment was repeated for at least three times, and comparable results were obtained.

Peptide Feeding, External Eye Assay, Climbing Ability Assay, and Lifespan Analysis Flies were raised at 25° C. on cornmeal medium supplemented with dry yeast. For climbing ability assay, third instar larvae were feed with 100 μM of TAT-P3L or TAT-P3LS1 dissolved in 2% sucrose solution for 2 h and then continued to culture in standard fly food. Eye images of 1 day-old adult of UAS-$(GGGGCC)_3$ or UAS-$(GGGGCC)_{36}$ flies were captured using a SPOT Insight CCD camera (Diagnostic instruments Inc.) on an Olympus SZX-12 stereomicroscope.

For lifespan and climbing ability assay, flies of 2dpe were feed with food containing different drug combination including vehicle control (ethanol), Mifepristone (RU486, 200 μM), RU486 (200 μM) plus TAT-P3L (50 μM), and RU486 (200 μM) plus TAT-P3LS1 (50 μM). Mifepristone (RU486, 200 μM) was used to induce transgene expression. For climbing ability assay, 10-15 flies were allocated to each experimental vials (total of 90-100 flies per condition) and monitored every 5 days. Fly climbing ability was analyzed by negative geotaxis. Groups of ∞15 flies were anesthetized and placed in a vertical plastic column. After 1 h recovery, flies were banged to the bottom, and then scored for climbing ability as the percentage of flies remaining at the bottom (<2 cm) at 25 s. Three trials were performed at 3 min intervals in each experiment. For lifespan analysis, 100-120 flies were tested per treatment as previously described[32].

Statistical Analyses

Data were analyzed by one-way ANOVA followed by post hoc Tukey test. "*", "", "*" and "****" represent $P<0.05$, $P<0.01$, $P<0.001$ and $P<0.0001$ respectively, which are considered statistically significant.

All patents, patent applications, and other publications, including GenBank Accession Numbers, cited in this application are incorporated by reference in the entirety for all purposes.

REFERENCES

1. DeJesus-Hernandez M, Mackenzie I R, Boeve B F, et al. Expanded GGGGCC hexanucleotide repeat in noncoding region of C9ORF72 causes chromosome 9p-linked FTD and ALS. *Neuron.* 2011; 72(2):245-256.
2. Renton A E, Majounie E, Waite A, et al. A hexanucleotide repeat expansion in C9ORF72 is the cause of chromosome 9p21-linked ALS-FTD. *Neuron.* 2011; 72(2):257-268.
3. Majounie E, Renton A E, Mok K, et al. Frequency of the C9orf72 hexanucleotide repeat expansion in patients with amyotrophic lateral sclerosis and frontotemporal dementia: A cross-sectional study. *Lancet Neurol.* 2012; 11(4): 323-330.
4. Beck J, Poulter M, Hensman D, et al. Large C9orf72 hexanucleotide repeat expansions are seen in multiple neurodegenerative syndromes and are more frequent than expected in the UK population. *Am J Hum Genet.* 2013; 92(3):345-353.
5. van Blitterswijk M, DeJesus-Hernandez M, Niemantsverdriet E, et al. Association between repeat sizes and clinical and pathological characteristics in carriers of C9ORF72 repeat expansions (xpansize-72): A cross-sectional cohort study. *Lancet Neurol.* 2013; 12(10):978-988.
6. Lee Y B, Chen H J, Peres J N, et al. Hexanucleotide repeats in ALS/FTD form length-dependent RNA foci, sequester RNA binding proteins, and are neurotoxic. *Cell Rep.* 2013; 5(5):1178-1186.
7. Haeusler A R, Donnelly C J, Periz G, et al. C9orf72 nucleotide repeat structures initiate molecular cascades of disease. *Nature.* 2014; 507(7491):195-200.
8. Donnelly C J, Zhang P W, Pham J T, et al. RNA toxicity from the ALS/FTD C9ORF72 expansion is mitigated by antisense intervention. *Neuron.* 2013; 80(2):415-428.
9. Tao Z, Wang H, Xia Q, et al. Nucleolar stress and impaired stress granule formation contribute to C9orf72 RAN translation-induced cytotoxicity. *Hum Mol Genet.* 2015; 24(9):2426-2441.
10. Mizielinska S, Gronke S, Niccoli T, et al. C9orf72 repeat expansions cause neurodegeneration in *drosophila* through arginine-rich proteins. *Science.* 2014; 345(6201): 1192-1194.
11. Vatovec S, Kovanda A, Rogelj B. Unconventional features of C9ORF72 expanded repeat in amyotrophic lateral sclerosis and frontotemporal lobar degeneration. *Neurobiol Aging.* 2014; 35(10):2421.e1-2421.e12.
12. Belzil V V, Bauer P O, Prudencio M, et al. Reduced C9orf72 gene expression in c9FTD/ALS is caused by histone trimethylation, an epigenetic event detectable in blood. *Acta Neuropathol.* 2013; 126(6): 895-905.
13. Mori K, Arzberger T, Grasser F A, et al. Bidirectional transcripts of the expanded C9orf72 hexanucleotide repeat are translated into aggregating dipeptide repeat proteins. *Acta Neuropathol.* 2013; 126(6):881-893.
14. Kearse M G, Todd P K. Repeat-associated non-AUG translation and its impact in neurodegenerative disease. *Neurotherapeutics.* 2014; 11(4):721-731.
15. Zu T, Gibbens B, Doty N S, et al. Non-ATG-initiated translation directed by microsatellite expansions. *Proc Natl Acad Sci USA.* 2011; 108(1):260-265.
16. Wang D B, Kinoshita C, Kinoshita Y, Morrison R S. P53 and mitochondrial function in neurons. *Biochim Biophys Acta.* 2014; 1842(8):1186-1197.
17. Zhang Y, Lu H. Signaling to p53: Ribosomal proteins find their way. *Cancer Cell.* 2009; 16(5):369-377.
18. Rickards B, Flint S J, Cole M D, LeRoy G. Nucleolin is required for RNA polymerase I transcription in vivo. *Mol Cell Biol.* 2007; 27(3):937-948.
19. Parlato R, Kreiner G. Nucleolar activity in neurodegenerative diseases: A missing piece of the puzzle? *J Mol Med (Berl).* 2013; 91(5):541-547.
20. Zhang Q, Tsoi H, Peng S, et al. Assessing a peptidylic inhibitor-based therapeutic approach that simultaneously suppresses polyglutamine RNA- and protein-mediated toxicities in patient cells and *drosophila*. *Dis Model Mech.* 2016; 9(3):321-334.
21. Arumugam S, Miller M C, Maliekal J, Bates P J, Trent J O, Lane A N. Solution structure of the RBD1,2 domains from human nucleolin. *J Biomol NMR.* 2010; 47(1):79-83.
22. Daubner G M, Clery A, Allain F H. RRM-RNA recognition: NMR or crystallography . . . and new findings. *Curr Opin Struct Biol.* 2013; 23(1):100-108.
23. Frankel A D, Pabo C O. Cellular uptake of the tat protein from human immunodeficiency virus. *Cell.* 1988; 55(6): 1189-1193.
24. Green M, Loewenstein P M. Autonomous functional domains of chemically synthesized human immunodeficiency virus tat trans-activator protein. *Cell.* 1988; 55(6): 1179-1188.
25. Fawell S, Seery J, Daikh Y, et al. Tat-mediated delivery of heterologous proteins into cells. *Proc Natl Acad Sci USA.* 1994; 91(2):664-668.
26. Vives E, Brodin P, Lebleu B. A truncated HIV-1 tat protein basic domain rapidly translocates through the plasma membrane and accumulates in the cell nucleus. *J Biol Chem.* 1997; 272(25):16010-16017.
27. Banez-Coronel M, Porta S, Kagerbauer B, et al. A pathogenic mechanism in huntington's disease involves small CAG-repeated RNAs with neurotoxic activity. *PLoS Genet.* 2012; 8(2):e1002481.
28. Gendron T F, Bieniek K F, Zhang Y J, et al. Antisense transcripts of the expanded C9ORF72 hexanucleotide repeat form nuclear RNA foci and undergo repeat-associated non-AUG translation in c9FTD/ALS. *Acta Neuropathol.* 2013; 126(6):829-844.
29. Avitabile D, Bailey B, Cottage C T, et al. Nucleolar stress is an early response to myocardial damage involving nucleolar proteins nucleostemin and nucleophosmin. *Proc Natl Acad Sci USA.* 2011; 108(15):6145-6150.
30. Yao Z, Duan S, Hou D, et al. B23 acts as a nucleolar stress sensor and promotes cell survival through its dynamic interaction with hnRNPU and hnRNPA1. *Oncogene.* 2010; 29(12): 1821-1834.
31. Shaltiel-Karyo R, Davidi D, Menuchin Y, et al. A novel, sensitive assay for behavioral defects in parkinson's disease model *drosophila*. *Parkinson Dis.* 2012; 2012: 697564.
32. Linford N J, Bilgir C, Ro J, Pletcher S D. Measurement of lifespan in *Drosophila Melanogaster*. *J Vis Exp.* 2013; (71). pii: 50068. doi(71):10.3791/50068.

What is claimed is:

1. A method for treating a poly(GA) disease, comprising administering to a subject in need thereof an effective amount of a polypeptide comprising SEQ ID NO:1 but not full length NCL protein.

2. The method of claim 1, wherein the polypeptide further comprises a heterologous amino acid sequence.

3. The method of claim 2, wherein the heterologous amino acid sequence is a cell-penetrating peptide.

4. The method of claim 2, wherein the polypeptide consists of SEQ ID NO:1, optionally with a TAT peptide at the N-terminus of the polypeptide.

5. The method of claim 1, wherein another therapeutic agent effective for treating a poly(GA) disease is co-administered to the subject.

6. The method of claim 1, wherein the polypeptide is administered orally, intravenously, intramuscularly, intraperitoneally, or subcutaneously.

7. The method of claim 1, wherein the subject has been diagnosed with a poly(GA) disease or is at risk of developing a poly(GA) disease.

8. The method of claim 1, wherein the polypeptide is administered once daily, weekly, or monthly.

9. A kit for treating a poly(GA) disease, comprising a first container containing a composition comprising (1) a polypeptide comprising SEQ ID NO:1 but not full length NCL protein, optionally further comprising, a heterologous amino acid sequence and (2) physiologically acceptable excipient; and a second container containing another therapeutic agent effective for treating a poly(GA) disease.

10. The kit of claim 9, further comprising informational material providing instructions on administration of the pharmaceutical composition.

* * * * *

SEQUENCE LISTING

<160> NUMBER OF SEQ ID NOS: 32

<210> SEQ ID NO 1
<211> LENGTH: 21
<212> TYPE: PRT
<213> ORGANISM: Artificial Sequence

```
<220> FEATURE:
<223> OTHER INFORMATION: synthetic nucleolin protein construct / PL3

<400> SEQUENCE: 1

Ala Glu Ile Arg Leu Val Ser Lys Asp Gly Lys Ser Lys Gly Ile Ala
1               5                   10                  15

Tyr Ile Glu Phe Lys
            20

<210> SEQ ID NO 2
<211> LENGTH: 13
<212> TYPE: PRT
<213> ORGANISM: Artificial Sequence
<220> FEATURE:
<223> OTHER INFORMATION: synthetic peptide construct P3

<400> SEQUENCE: 2

Asp Gly Lys Ser Lys Gly Ile Ala Tyr Ile Glu Phe Lys
1               5                   10

<210> SEQ ID NO 3
<211> LENGTH: 77
<212> TYPE: PRT
<213> ORGANISM: Artificial Sequence
<220> FEATURE:
<223> OTHER INFORMATION: synthetic RNA recognition motif (RRM1) of
      nucleolin protein construct

<400> SEQUENCE: 3

Phe Asn Leu Phe Ile Gly Asn Leu Asn Pro Asn Lys Ser Val Ala Glu
1               5                   10                  15

Leu Lys Val Ala Ile Ser Glu Pro Phe Ala Lys Asn Asp Leu Ala Val
            20                  25                  30

Val Asp Val Arg Thr Gly Thr Asn Arg Lys Phe Gly Tyr Val Asp Phe
        35                  40                  45

Glu Ser Ala Glu Asp Leu Glu Lys Ala Leu Glu Leu Thr Gly Leu Lys
    50                  55                  60

Val Phe Gly Asn Glu Ile Lys Leu Glu Lys Pro Lys Gly
65                  70                  75

<210> SEQ ID NO 4
<211> LENGTH: 74
<212> TYPE: PRT
<213> ORGANISM: Artificial Sequence
<220> FEATURE:
<223> OTHER INFORMATION: synthetic RNA recognition motif (RRM2) of
      nucleolin protein construct

<400> SEQUENCE: 4

Arg Thr Leu Leu Ala Lys Asn Leu Ser Phe Asn Ile Thr Glu Asp Glu
1               5                   10                  15

Leu Lys Glu Val Phe Glu Asp Ala Leu Glu Ile Arg Leu Val Ser Gln
            20                  25                  30

Asp Gly Lys Ser Lys Gly Ile Ala Tyr Ile Glu Phe Lys Ser Glu Ala
        35                  40                  45

Asp Ala Glu Lys Asn Leu Glu Glu Lys Gln Gly Ala Glu Ile Asp Gly
    50                  55                  60

Arg Ser Val Ser Leu Tyr Tyr Thr Gly Glu
65                  70
```

```
<210> SEQ ID NO 5
<211> LENGTH: 75
<212> TYPE: PRT
<213> ORGANISM: Artificial Sequence
<220> FEATURE:
<223> OTHER INFORMATION: synthetic RNA recognition motif (RRM3) of
      nucleolin protein construct

<400> SEQUENCE: 5

Lys Thr Leu Val Leu Ser Asn Leu Ser Tyr Ser Ala Thr Glu Glu Thr
1               5                   10                  15

Leu Gln Glu Val Phe Glu Lys Ala Thr Phe Ile Lys Val Pro Gln Asn
            20                  25                  30

Gln Gln Gly Lys Ser Lys Gly Tyr Ala Phe Ile Glu Phe Ala Ser Phe
        35                  40                  45

Glu Asp Ala Lys Glu Ala Leu Asn Ser Cys Asn Lys Met Glu Ile Glu
    50                  55                  60

Gly Arg Thr Ile Arg Leu Glu Leu Gln Gly Pro
65                  70                  75

<210> SEQ ID NO 6
<211> LENGTH: 11
<212> TYPE: PRT
<213> ORGANISM: Artificial Sequence
<220> FEATURE:
<223> OTHER INFORMATION: synthetic peptide construct TAT

<400> SEQUENCE: 6

Tyr Gly Arg Lys Lys Arg Arg Gln Arg Arg
1               5                   10

<210> SEQ ID NO 7
<211> LENGTH: 22
<212> TYPE: PRT
<213> ORGANISM: Artificial Sequence
<220> FEATURE:
<223> OTHER INFORMATION: synthetic peptide construct TAT-RRM1-P1

<400> SEQUENCE: 7

Tyr Gly Arg Lys Lys Arg Arg Gln Arg Arg Thr Gly Thr Asn Arg
1               5                   10                  15

Lys Phe Gly Tyr Val Asp
            20

<210> SEQ ID NO 8
<211> LENGTH: 32
<212> TYPE: PRT
<213> ORGANISM: Artificial Sequence
<220> FEATURE:
<223> OTHER INFORMATION: synthetic peptide construct TAT-RRM2-P1
      (TAT-P3L)

<400> SEQUENCE: 8

Tyr Gly Arg Lys Lys Arg Arg Gln Arg Arg Ala Glu Ile Arg Leu
1               5                   10                  15

Val Ser Lys Asp Gly Lys Ser Lys Gly Ile Ala Tyr Ile Glu Phe Lys
            20                  25                  30

<210> SEQ ID NO 9
<211> LENGTH: 29
<212> TYPE: PRT
<213> ORGANISM: Artificial Sequence
<220> FEATURE:
<223> OTHER INFORMATION: synthetic peptide construct TAT-RRM3-P1
```

-continued

```
<400> SEQUENCE: 9

Tyr Gly Arg Lys Lys Arg Arg Gln Arg Arg Thr Phe Ile Lys Val
1               5                   10                  15

Pro Gln Asn Gln Asn Gly Lys Ser Lys Gly Tyr Ala Phe
            20                  25

<210> SEQ ID NO 10
<211> LENGTH: 31
<212> TYPE: PRT
<213> ORGANISM: Artificial Sequence
<220> FEATURE:
<223> OTHER INFORMATION: synthetic peptide construct TAT-RRM4-P1

<400> SEQUENCE: 10

Tyr Gly Arg Lys Lys Arg Arg Gln Arg Arg Arg Ala Arg Ile Val
1               5                   10                  15

Thr Asp Arg Glu Thr Gly Ser Ser Lys Gly Phe Gly Phe Val Asp
            20                  25                  30

<210> SEQ ID NO 11
<211> LENGTH: 21
<212> TYPE: PRT
<213> ORGANISM: Artificial Sequence
<220> FEATURE:
<223> OTHER INFORMATION: synthetic peptide construct P3LS1

<400> SEQUENCE: 11

Gly Gly Glu Asp Ile Lys Ser Arg Val Glu Ala Ala Ser Ile Leu Tyr
1               5                   10                  15

Phe Ile Lys Lys Lys
            20

<210> SEQ ID NO 12
<211> LENGTH: 6
<212> TYPE: DNA
<213> ORGANISM: Artificial Sequence
<220> FEATURE:
<223> OTHER INFORMATION: synthetic hexanucleotide repeat sequence

<400> SEQUENCE: 12 ggggcc                                                             6

<210> SEQ ID NO 13
<211> LENGTH: 15
<212> TYPE: DNA
<213> ORGANISM: Artificial Sequence
<220> FEATURE:
<223> OTHER INFORMATION: synthetic nucleotide TYE563-labeled LNA probe
      sequence
<220> FEATURE:
<221> NAME/KEY: misc_feature
<222> LOCATION: (1)..(1)
<223> OTHER INFORMATION: 5' Cytosine labeled with TYE563

<400> SEQUENCE: 13
cccggccccg gcccc                                                  15

<210> SEQ ID NO 14
<211> LENGTH: 21
<212> TYPE: PRT
<213> ORGANISM: Artificial Sequence
<220> FEATURE:
<223> OTHER INFORMATION: synthetic peptide mutant PL3MT1
```

-continued

```
<400> SEQUENCE: 14

Ala Ala Ile Arg Leu Val Ser Lys Asp Gly Lys Ser Lys Gly Ile Ala
1               5                   10                  15

Tyr Ile Glu Phe Lys
            20

<210> SEQ ID NO 15
<211> LENGTH: 21
<212> TYPE: PRT
<213> ORGANISM: Artificial Sequence
<220> FEATURE:
<223> OTHER INFORMATION: synthetic peptide mutant PL3MT2

<400> SEQUENCE: 15

Ala Glu Ala Arg Leu Val Ser Lys Asp Gly Lys Ser Lys Gly Ile Ala
1               5                   10                  15

Tyr Ile Glu Phe Lys
            20

<210> SEQ ID NO 16
<211> LENGTH: 21
<212> TYPE: PRT
<213> ORGANISM: Artificial Sequence
<220> FEATURE:
<223> OTHER INFORMATION: synthetic peptide mutant PL3MT3

<400> SEQUENCE: 16

Ala Glu Ile Ala Leu Val Ser Lys Asp Gly Lys Ser Lys Gly Ile Ala
1               5                   10                  15

Tyr Ile Glu Phe Lys
            20

<210> SEQ ID NO 17
<211> LENGTH: 21
<212> TYPE: PRT
<213> ORGANISM: Artificial Sequence
<220> FEATURE:
<223> OTHER INFORMATION: synthetic peptide mutant PL3MT4

<400> SEQUENCE: 17

Ala Glu Ile Arg Ala Val Ser Lys Asp Gly Lys Ser Lys Gly Ile Ala
1               5                   10                  15

Tyr Ile Glu Phe Lys
            20

<210> SEQ ID NO 18
<211> LENGTH: 21
<212> TYPE: PRT
<213> ORGANISM: Artificial Sequence
<220> FEATURE:
<223> OTHER INFORMATION: synthetic peptide mutant PL3MT5

<400> SEQUENCE: 18

Ala Glu Ile Arg Leu Ala Ser Lys Asp Gly Lys Ser Lys Gly Ile Ala
1               5                   10                  15

Tyr Ile Glu Phe Lys
            20

<210> SEQ ID NO 19
<211> LENGTH: 21
<212> TYPE: PRT
<213> ORGANISM: Artificial Sequence
<220> FEATURE:
<223> OTHER INFORMATION: synthetic peptide mutant PL3MT6
```

```
<400> SEQUENCE: 19

Ala Glu Ile Arg Leu Val Ala Lys Asp Gly Lys Ser Lys Gly Ile Ala
1               5                   10                  15

Tyr Ile Glu Phe Lys
            20

<210> SEQ ID NO 20
<211> LENGTH: 21
<212> TYPE: PRT
<213> ORGANISM: Artificial Sequence
<220> FEATURE:
<223> OTHER INFORMATION: synthetic peptide mutant PL3MT7

<400> SEQUENCE: 20

Ala Glu Ile Arg Leu Val Ser Ala Asp Gly Lys Ser Lys Gly Ile Ala
1               5                   10                  15

Tyr Ile Glu Phe Lys
            20

<210> SEQ ID NO 21
<211> LENGTH: 21
<212> TYPE: PRT
<213> ORGANISM: Artificial Sequence
<220> FEATURE:
<223> OTHER INFORMATION: synthetic peptide mutant PL3MT8

<400> SEQUENCE: 21

Ala Glu Ile Arg Leu Val Ser Lys Ala Gly Lys Ser Lys Gly Ile Ala
1               5                   10                  15

Tyr Ile Glu Phe Lys
            20

<210> SEQ ID NO 22
<211> LENGTH: 21
<212> TYPE: PRT
<213> ORGANISM: Artificial Sequence
<220> FEATURE:
<223> OTHER INFORMATION: synthetic peptide mutant PL3MT9

<400> SEQUENCE: 22

Ala Glu Ile Arg Leu Val Ser Lys Asp Ala Lys Ser Lys Gly Ile Ala
1               5                   10                  15

Tyr Ile Glu Phe Lys
            20

<210> SEQ ID NO 23
<211> LENGTH: 21
<212> TYPE: PRT
<213> ORGANISM: Artificial Sequence
<220> FEATURE:
<223> OTHER INFORMATION: synthetic peptide mutant PL3MT10

<400> SEQUENCE: 23

Ala Glu Ile Arg Leu Val Ser Lys Asp Gly Ala Ser Lys Gly Ile Ala
1               5                   10                  15

Tyr Ile Glu Phe Lys
            20

<210> SEQ ID NO 24
<211> LENGTH: 21
<212> TYPE: PRT
<213> ORGANISM: Artificial Sequence
<220> FEATURE:
<223> OTHER INFORMATION: synthetic peptide mutant PL3MT11
```

-continued

```
<400> SEQUENCE: 24

Ala Glu Ile Arg Leu Val Ser Lys Asp Gly Lys Ala Lys Gly Ile Ala
1               5                   10                  15

Tyr Ile Glu Phe Lys
            20

<210> SEQ ID NO 25
<211> LENGTH: 21
<212> TYPE: PRT
<213> ORGANISM: Artificial Sequence
<220> FEATURE:
<223> OTHER INFORMATION: synthetic peptide mutant PL3MT12

<400> SEQUENCE: 25

Ala Glu Ile Arg Leu Val Ser Lys Asp Gly Lys Ser Ala Gly Ile Ala
1               5                   10                  15

Tyr Ile Glu Phe Lys
            20

<210> SEQ ID NO 26
<211> LENGTH: 21
<212> TYPE: PRT
<213> ORGANISM: Artificial Sequence
<220> FEATURE:
<223> OTHER INFORMATION: synthetic peptide mutant PL3MT13

<400> SEQUENCE: 26

Ala Glu Ile Arg Leu Val Ser Lys Asp Gly Lys Ser Lys Ala Ile Ala
1               5                   10                  15

Tyr Ile Glu Phe Lys
            20

<210> SEQ ID NO 27
<211> LENGTH: 21
<212> TYPE: PRT
<213> ORGANISM: Artificial Sequence
<220> FEATURE:
<223> OTHER INFORMATION: synthetic peptide mutant PL3MT14

<400> SEQUENCE: 27

Ala Glu Ile Arg Leu Val Ser Lys Asp Gly Lys Ser Lys Gly Ala Ala
1               5                   10                  15

Tyr Ile Glu Phe Lys
            20

<210> SEQ ID NO 28
<211> LENGTH: 21
<212> TYPE: PRT
<213> ORGANISM: Artificial Sequence
<220> FEATURE:
<223> OTHER INFORMATION: synthetic peptide mutant PL3MT15

<400> SEQUENCE: 28

Ala Glu Ile Arg Leu Val Ser Lys Asp Gly Lys Ser Lys Gly Ile Ala
1               5                   10                  15

Ala Ile Glu Phe Lys
            20

<210> SEQ ID NO 29
<211> LENGTH: 21
<212> TYPE: PRT
<213> ORGANISM: Artificial Sequence
<220> FEATURE:
<223> OTHER INFORMATION: synthetic peptide mutant PL3MT16
```

```
-continued

<400> SEQUENCE: 29

Ala Glu Ile Arg Leu Val Ser Lys Asp Gly Lys Ser Lys Gly Ile Ala
1               5                   10                  15

Tyr Ala Glu Phe Lys
            20

<210> SEQ ID NO 30
<211> LENGTH: 21
<212> TYPE: PRT
<213> ORGANISM: Artificial Sequence
<220> FEATURE:
<223> OTHER INFORMATION: synthetic peptide mutant PL3MT17

<400> SEQUENCE: 30

Ala Glu Ile Arg Leu Val Ser Lys Asp Gly Lys Ser Lys Gly Ile Ala
1               5                   10                  15

Tyr Ile Ala Phe Lys
            20

<210> SEQ ID NO 31
<211> LENGTH: 21
<212> TYPE: PRT
<213> ORGANISM: Artificial Sequence
<220> FEATURE:
<223> OTHER INFORMATION: synthetic peptide mutant PL3MT18

<400> SEQUENCE: 31

Ala Glu Ile Arg Leu Val Ser Lys Asp Gly Lys Ser Lys Gly Ile Ala
1               5                   10                  15

Tyr Ile Glu Ala Lys
            20

<210> SEQ ID NO 32
<211> LENGTH: 21
<212> TYPE: PRT
<213> ORGANISM: Artificial Sequence
<220> FEATURE:
<223> OTHER INFORMATION: synthetic peptide mutant PL3MT19

<400> SEQUENCE: 32

Ala Glu Ile Arg Leu Val Ser Lys Asp Gly Lys Ser Lys Gly Ile Ala
1               5                   10                  15

Tyr Ile Glu Phe Ala
            20
```